US008820662B2

(12) United States Patent
Yeates

(10) Patent No.: US 8,820,662 B2
(45) Date of Patent: Sep. 2, 2014

(54) NOZZLE AND NOZZLE HOLDER FOR AN AEROSOL GENERATOR

(76) Inventor: Donovan B. Yeates, Escondido, CA (US)

( * ) Notice: Subject to any disclaimer, the term of this patent is extended or adjusted under 35 U.S.C. 154(b) by 808 days.

(21) Appl. No.: 12/890,302

(22) Filed: Sep. 24, 2010

(65) Prior Publication Data

US 2011/0011899 A1 Jan. 20, 2011

Related U.S. Application Data

(63) Continuation-in-part of application No. 11/315,951, filed on Dec. 22, 2005, now Pat. No. 7,802,569.

(51) Int. Cl.

| | |
|---|---|
| ***B05B 7/10*** | (2006.01) |
| ***B05B 7/06*** | (2006.01) |
| ***B05B 1/26*** | (2006.01) |
| ***A61M 15/00*** | (2006.01) |
| ***B01D 45/08*** | (2006.01) |
| *A61M 16/00* | (2006.01) |
| *A61M 11/06* | (2006.01) |

(52) U.S. Cl.

CPC ......... *A61M 15/0086* (2013.01); *A61M 15/008* (2013.01); *B01D 45/08* (2013.01); *A61M 2016/0036* (2013.01); *A61M 2205/368* (2013.01); *A61M 2205/362* (2013.01); *B05B 7/065* (2013.01); *A61M 11/06* (2013.01)

USPC ....... 239/399; 239/406; 239/424; 128/200.18

(58) Field of Classification Search

CPC ........ B05B 7/10; B05B 7/0408; B05B 15/06; F23D 11/10; F23D 11/102; B01F 5/0057; F16M 13/00

USPC ......... 239/399, 594, 595, 406, 418, 423, 424; 128/200.18, 200.23, 203.12, 203.15

See application file for complete search history.

(56) References Cited

U.S. PATENT DOCUMENTS 3,266,736 A * 8/1966 Lankford ...................... 239/408
4,852,561 A * 8/1989 Sperry ..................... 128/200.23

(Continued)

FOREIGN PATENT DOCUMENTS

| | | |
|---|---|---|
| GB | 2342874 | 4/2000 |
| WO | 0221100 | 3/2002 |

(Continued)

OTHER PUBLICATIONS

Extended Search Report issued by the European Patent Office for EP 06 848 085.4, dated Mar. 10, 2010.

Kim et al. Multijet and Multistage Aerosol Concentrator:Design and Performance Analysis, Journal of Aerosol Medicine, vol. 14, No. 2, 2001. pp. 245-254.

Barr et al. Aerosol Concentrator: Design, Construction Calibration, and Use , Aerosol Science and Technology, 1983, 2: 437-442.

Office Action issued by the United States Patent and Trademark Office for U.S. Appl. No. 11/315,951 dated Apr. 28, 2009.

(Continued)

*Primary Examiner* — Len Tran
*Assistant Examiner* — Chee-Chong Lee
(74) *Attorney, Agent, or Firm* — Schlee IP International, P.C.; Alexander R. Schlee

(57) ABSTRACT

A nozzle for generating an aerosol from a fluid and a gas is described. The nozzle comprises at least one wettable cone-shaped gas exit channel that widens in a direction of gas flow from a cone apex to a cone base of the wettable cone-shaped gas exit channel and is connected at the cone apex to a nozzle gas supply channel. The nozzle further comprises at least one annular fluid exit port at the circumference of the cone base that is connected to a nozzle fluid supply channel. Further, a nozzle holder is described. The nozzle holder comprises a cylindrical crown comprises a plurality of circumferentially spaced grooves that are connected to the ring-shaped fluid exit port.

17 Claims, 10 Drawing Sheets

DETAIL T
SCALE 6 : 1

(56) References Cited

U.S. PATENT DOCUMENTS

| | | | | |
|---|---|---|---|---|
| 5,025,806 | A * | 6/1991 | Palmer et al. | 128/203.12 |
| 5,474,059 | A * | 12/1995 | Cooper | 128/200.22 |
| 5,522,385 | A | 6/1996 | Lloyd et al. | |
| 5,533,406 | A | 7/1996 | Geise | |
| 5,630,409 | A * | 5/1997 | Bono et al. | 128/200.18 |
| 5,800,598 | A | 9/1998 | Chein et al. | |
| 5,823,434 | A * | 10/1998 | Cooper | 239/102.2 |
| 5,845,846 | A * | 12/1998 | Watanabe et al. | 239/8 |
| 5,906,202 | A | 5/1999 | Schuster et al. | |
| 6,116,516 | A * | 9/2000 | Ganan-Calvo | 239/8 |
| 6,158,431 | A | 12/2000 | Poole | |
| 6,234,167 | B1 * | 5/2001 | Cox et al. | 128/200.14 |
| 6,367,471 | B1 | 4/2002 | Genosar et al. | |
| 6,929,005 | B2 * | 8/2005 | Sullivan et al. | 128/203.21 |
| 7,802,569 | B2 | 9/2010 | Yeates et al. | |
| 8,375,987 | B2 | 2/2013 | Yeates et al. | |
| 2004/0016427 | A1 | 1/2004 | Byron et al. | |
| 2004/0187869 | A1 | 9/2004 | Bjorndal et al. | |
| 2005/0196345 | A1 | 9/2005 | Diederichs et al. | |

FOREIGN PATENT DOCUMENTS

| | | |
|---|---|---|
| WO | 2005052288 | 6/2005 |
| WO | 2012039720 | 3/2012 |

OTHER PUBLICATIONS

Reply to Office Action issued Apr. 28, 2009 filed Sep. 28, 2009 in the United States Patent and Trademark Office for U.S. Appl. No. 11/315,951.

Office Action issued by the United States Patent and Trademark Office for U.S. Appl. No. 11/315,951 dated Jan. 6, 2010.

Reply to Office Action issued Jan. 6, 2010 filed Mar. 4, 2010 in the United States Patent and Trademark Office for U.S. Appl. No. 11/315,951.

Request for Continued Examination, preliminary amendment and declaration filed Mar. 24, 2010 in the United States Patent and Trademark Office for U.S. Appl. No. 11/315,951.

Notice of Allowance issued by the United States Patent and Trademark Office for U.S. Appl. No. 11/315,951 dated May 20, 2010.

Notification of transmittal of the International Search Report and the Written Opinion of the International Searching Authority, or the Declaration in PCT/US2010/050303 dated Jul. 29, 2011.

Notice of Allowance issued in pending U.S. Appl. No. 12/889,903 issued Aug. 5, 2013.

Notice of Allowance issued in pending U.S. Appl. No. 12/890,376 issued Sep. 18, 2013.

* cited by examiner

SECTION M-M
SCALE 1.5 : 1

SECTION M-M
SCALE 1 : 1.2

3235
3233
3205
3211
3300
3216
3214
3212
3204
3210

3205
3230
3240
3215
3209
3214
3213
3211
3206
3204
3234
DETAIL T
SCALE 6 : 1

2005
3203
2007
3208
3203
3001
3220
3206
SECTION R-R

3205
T
3206
3202
2008
3007
3204
3234
3204
SECTION P-P
3201
3208

R
R

2007
P
P
0 to .030 INCHES
3001
3301

SECTION Y-Y

SECTION H-H
SCALE 1 : 1.5

SECTION F-F
SCALE 1 : 3

SECTION J-J
SCALE 1 : 3

SECTION J-J
SCALE 1 : 4

SECTION K-K
SCALE 1 : 2

SECTION H-H
SCALE 1 : 3

NOZZLE AND NOZZLE HOLDER FOR AN AEROSOL GENERATOR

CROSS-REFERENCE TO RELATED APPLICATIONS

This application is a Continuation-in-part patent application claiming the benefit of the U.S. non-provisional patent application Ser. No. 11/315,951 filed on Dec. 22, 2005 now U.S. Pat. No. 7,802,569 and published under the publication No. US-2007-0144514-A1 on Jun. 28, 2007. This prior non-provisional patent application Ser. No. 11/315,951 is herewith incorporated in its entirety by reference.

GOVERNMENT SUPPORT

The present invention was made with U.S. Government support from the National Institutes of Health, National Heart, Lung, and Blood Institute, under grant No. HL78281. The U.S. Government has certain rights in this invention.

BACKGROUND OF THE INVENTION

The present disclosure relates to a compact portable device for the generation of concentrated respirable dry particles from an aqueous solution or suspension.

There is an ever increasing need to deliver large masses of biologics and other agents to the respiratory tract by aerosol. Many devices which generate liquid aerosols may not work well with molecules of high molecular weight or at high concentrations. In addition, some of these devices may degrade the molecules during aerosolization. These limitations, together with the need to reduce the use of fluorocarbons, have lead to the development of dry powder inhalers. In these devices a "blister" or capsule containing the drug is broken and the powdered drug together with the included excipients is dispersed using a vortex caused by inhalation or aerosolized by some other mechanical means such as sonication. Excipients are added to the active agent to aid in the aerosolization of these agglomerates. In some cases, such as Exhubra, they comprise some 70% of the mass of the mixture. The use of excipients results in increased formulation costs, safety pharmacology costs and potential unwanted side effects. These dry powers containing the active agent are most often generated using a spray-drying process. Spray driers have been in common use for many years. Generally they consist of generating an aerosol at the top of a vertical cylindrical tower in which the aerosol spray is diluted with warm gas that may be in the same direction as the spray or in the opposite direction. A cyclone at the output is used to collect the resulting powder. Excipients are added to the collected powders to aid in their dispersion. This mixture is placed in a dry power inhaler, DPI. There are several limitations with this approach:

a) The stored resultant dry particles must be stable and preferably resistant to high humidity.

b) They must be formulated with excipients such as to be easily dispersed c) The size of the drug particles is generally smaller than that of the excipient particles when the two chemicals are in discrete form.

d) The maximum which can be inhaled is limited to the size of the capsule not the volume of the inhalation.

e) The spray dry process is likely 60% efficient and the delivery to the lungs by the dry power inhaler 30% efficient resulting in losses of some 80% of the active agent.

f) A rapid inhalation results in most of the powder in the capsule being aerosolized but results in high mouth and throat deposition. A slow inhalation can result in higher deep lung deposition but a low efficiency of aerosolization of the powder in the capsule. These issues lead to wide variability in the dose administered leading to both efficacy and safety concerns.

These issues can be overcome by a device which generates a liquid aerosol containing the active agent, dries it, concentrates and delivers the residual dry aerosol of the active agent to the lungs in one continuous set of processes such as described in this disclosure. It should be recognized that even the instruments which are of laboratory rather than commercial size are 70 inches tall and weigh 50-80 kg. Of note, the spray towers in all these instruments are vertically orientated. A compact clinical device would be best served by a small horizontal drying chamber.

Delivery of higher masses to the lungs than can be obtained with solid particles of drug can be achieved with aerosols of the same aerodynamic diameter that have a particle density of less than 1 (Edwards 1996). The formulation of such particles have been the subject of a number of patents, including, U.S. Pat. No. (7,435,408). Large porous particles have been produced by spray drying a mixture of polyester and an active agent such as insulin. These spray dried aerosols have generally been produced by standard spray drying techniques and collected as a powder. To produce particles with a low density, a liquid which has a small molecular weight as compared to a much larger molecular weight additive in the solvent evaporates faster than the diffusion of the large molecular weight component. The resulting particles may be either hollow or have open gas spaces making the geometrical diameter larger than the aerodynamic diameter. These aerosols are generally collected using a cyclone. The powders so produced must later be reaerosolized to be inhaled by the patient. As noted, using such techniques only a small fraction of the original drug is delivered to the lungs. The present disclosure describes how the dilution of a plume of aerosol can be rapidly diluted near to its origin of formation using a heated counter-flow gas jet coaxial in opposite direction to that of the aerosol plume. In addition an annulus of dilution gas transports the aerosol away from the generator along an evaporation chamber to a virtual concentrator. The present disclosure also describes how the evaporation of these aqueous particles in this disturbed plume can be augmented by provision of infrared radiation from a source outside the evaporation chamber.

The United States non-provisional patent application Ser. No. 11/315,951 filed on Dec. 22, 2005 and published under the publication no. US-2007-0144514-A1 (Yeates et al.), the benefit of which is claimed for the present application, has described a dry power aerosol generator and processing system whereby aqueous solutions of agents are aerosolized, evaporated, concentrated and delivered as a dry power aerosol comprised entirely of the dissolved solute. In the present disclosure are described details of improvements to that system and the subsequent novel findings regarding the generation of pure protein respirable aerosols with a density less than one in a compact device. This device eliminates the need for spray-drying, collection with a cyclone, mixing with excipients and placing in a dry powder inhaler. The improvements to that system are detailed within. The marked reduction of internal gas flow resistance has enabled the use of a blower that is only 2×2×1 inch, thus increasing the portability of the device. Easy to assembly friction fit designs eliminated the use of large O-ring seals on the evaporation chamber making it much easier to assemble by a sick patient. Light weight heaters with resistance to flow as well as a low thermal inertia were developed to allow functionality within a minute of turning on and increase the portability. The counter-flow tube was centered within the concentrator to ensure easy assembly and accurate alignment with the axis of the aerosol jet thus increasing the reliability of its performance. An additional heating element for the warming of the gas for the nozzle and the counter-flow has been included enabling more rapid evaporation of the aerosol plume. Focusing reflectors have been included on the infrared heat source to lower the power needed for the infrared heater. This and the above modifications reduce the overall power used by the device. These and other functional and practical improvements have been disclosed herein. In concert they make the device more portable, more functional, easier and more cost effective to manufacture and provide new possibilities for the generation of novel particles for immediate inhalation that was not previously possible.

Virtual impaction has been used as a means to concentrate aerosols (U.S. Pat. No. 4,767,524, Pillai and Yeates, 1994). There have been several modifications of these designs, including the use of slit orifices in place of round orifices (Marple and Robow 1986). Yeates' patent application 200701445 uses this information to design a concentrator with radial slits for a cut-off diameter of 2.5 micron. The present disclosure shows how to concentrate the major mass of particles within the respiratory range. This range is typically 1-5 micron but may cover the range of 0.5-10 micron. According to Marple and Robow, to capture particles above 1 micron a 1 mm orifice slit is required compared to a 2.6 mm slit to concentrate particles above 2.5 micrometers. This potentially increases the pressure head required to accelerate the aerosol through the slits. To reduce the pressure head upstream of the concentrator, parabolic entrances to the orifices were incorporated into the design. It is notable that Seshadri, American Association for Aerosol Research (AAAR) 2006, teaches the use of a parabolic entry profile together with a sheath gas flow to reduce wall losses and potentially enhance the concentration factor. As noted, in this present disclosure they are incorporated to reduce the upstream pressure required to operate the concentrator. Shekarrizz, U.S. Pat. No. 7,178,380 describes a concentrator with concave and convex accelerator walls together with a side injector port they claim reduces clogging. That concentrator utilizes input flow rates of 15 liters/minute, just a small fraction of the flow rates in the present device which are typically between 10 was amended in 0 and 300 liters per minute but higher and lower flow rates are possible in this disclosed device. The present device does not have, nor does it require, the proposed injector ports to prevent clogging. Alternatively, U.S. Pat. Nos. 7,261,007 and 5,858,043 describe concentric slits to reduce end effects. When concentric slits are used it is much more difficult to exhaust the gas than using the present compact design.

A first object of the present disclosure is to provide the means, in a small practical device, to generate an aqueous (or other solvent with a high vapor pressure) aerosol and by dilution and heating, rapidly evaporate aqueous aerosols and thereafter to concentrate the resultant particles and deliver them at flow rates compatible with the full range of normal inspiratory flows.

A second object of the present disclosure is to eliminate high pressure couplings so the device can be easily assembled and disassembled for cleaning.

A third object of the invention is to lower the resistance to gas flow through the device to enable the construction of a small device using a small blower to provide the dilution gas.

A fourth object of the present disclosure is to minimize leakage of gas and/or aerosol between the various components of the device while maintaining structure integrity junction between each of the components.

A fifth object of the present disclosure is to facilitate the provision of a counter-flow gas that is precisely coaxial with the aerosol plume and of opposite direction to the aerosol plume.

A sixth object of the present disclosure is to provide heated compressed gas to both the nozzle and the counter-flow tube while minimizing heat losses.

A seventh object of the present disclosure is to provide, from a source outside the evaporation chamber, localized radiant heat to the newly formed aqueous aerosol particles at the wavelength of the maximum infrared absorption for water.

An eighth object of the present disclosure is to allow the device to be used with different easily interchangeable nozzle-holder configurations that enable compressed gas either to be delivered through a central orifice or surround a central fluid stream.

A ninth object of the present disclosure is to have these nozzle-holders keyed for use in the flow conditioner and to have the ability to include a compressible fluid reservoir in place of a fluid inlet.

A tenth object of the present disclosure is, in a compact device, to provide for a high velocity gas stream to be heated while it flows in one direction and then provide a uniform lower velocity flow in the opposite direction while allowing for the perturbations caused by an aerosol plume and counter-flow gas.

An eleventh object of the present disclosure is to efficiently concentrate a respirable aerosol larger than 0.5 micron with minimal pressure drop between the input and the exhaust gas.

A twelfth object of the present disclosure is to facilitate easy assembly and disassembly while maintaining axial and rotational high precision alignment.

A thirteenth object of the present disclosure is to prevent any aerosol particles in the concentrator exhaust gas stream from contaminating the atmosphere.

A fourteenth object of the present disclosure is to minimize any aerosol deposition due to turbulence at the output of the concentrator.

A fifteenth object of the present disclosure is to provide an efficient means of delivering the concentrated aerosol at the output by means of the parabolic shaped nature of the output cone.

A sixteenth object of the present disclosure is to provide a concentrated aerosol at a small positive pressure to provide a pressure-assist for patients who have trouble generating sufficient inspiratory pressure and flow to trigger some other dry powder inhalers.

SUMMARY OF THE INVENTION

These and other objects are achieved according to a first aspect of the present invention by a nozzle for generating an aerosol from a fluid and a gas, the nozzle comprising: at least one wettable cone-shaped gas exit channel that widens in a direction of gas flow from a cone apex to a cone base of the wettable cone-shaped gas exit channel and is connected at the cone apex to a nozzle gas supply channel; and at least one annular fluid exit port at the circumference of the cone base that is connected to a nozzle fluid supply channel.

These and other objects are achieved according to a second aspect of the present invention by a nozzle holder comprising a first end with a nozzle holder fluid inlet port and a second end comprising the aforementioned nozzle. The nozzle holder further comprises a barrel with a cylindrical barrel hole with an inner cylindrical barrel hole and an inner cylindrical barrel diameter, and a nozzle body comprising the stem and a cylindrical crown comprising an outer cylindrical crown surface snugly fit into the cylindrical barrel hole wall, wherein the cylindrical crown comprises a plurality of circumferentially spaced grooves that are connected to the ring-shaped fluid exit port.

DETAILED DESCRIPTION OF THE INVENTION

According to a preferred embodiment of the nozzle of the invention, the nozzle further comprises a cylindrical stem having an outer stem wall having an outer stem diameter; and an annulus having an annulus hole wall comprising an inner annulus diameter that is slightly larger than the outer stem diameter; wherein the cylindrical stem extends through the annulus hole and comprises the wettable cone-shaped gas exit channel; and the annular fluid exit port is formed by an annular gap between the annulus hole wall and the outer stem wall. Preferably, the diameter difference between the inner annulus diameter and the outer stem diameter is between 0.006 and 0.8 mm resulting in an annular gap width between the 0.003 and 0.4 mm. This allows benefiting from the capillary forces for the fluid transfer from the nozzle to in location where the fluid is aerosolized.

According to another preferred embodiment of the nozzle of the invention, the annulus comprises a front face that extends substantially perpendicular to the annular fluid exit port. This annulus allows easy assembly and allows to manufacture the annulus separately from the remaining parts of the nozzle so that its inner diameter can be exactly manufactured as needed for maintaining small tolerances between the annulus hole and the stem so that the nozzle benefits from the capillary forces. However, in the alternative, it is also possible to integrate this part as an integral part of a nozzle holder or barrel.

According to another preferred embodiment of the nozzle of the invention, the stem protrudes by 0-1 mm beyond the front face of the annulus. This can be advantageous for the fluid to advance to a circular lip formed at the forward edge of the stem. However, also such designs comprising a stem that is flush with the front face of the annulus or even recessed in comparison to the front face of the annulus are possible.

According to another preferred embodiment of the nozzle of the invention, the front face of the annulus is hydrophobic while the annulus hole wall and the outer stem wall are readily wettable by the fluid. This is advantageous for guiding the fluid to the location where it is transformed into an aerosol. However, in the alternative, also regular surfaces are possible and the guidance of the fluid to the location where it is aerosolized may work simply by pressure differentials and/or capillary action so that no specifically readily wettable or hydrophobic surfaces are needed.

According to another preferred embodiment of the nozzle of the invention, a diameter of the cone base of a wettable cone-shaped gas exit channel equals substantially the entire outer stem diameter so that the stem terminates in a sharp annular lip at the cone base of the wettable cone-shaped gas exit channel. This allows the fluid to flow readily through the gap between the stem and annulus over the lip into the cone, both by capillary forces and by pressure differentials, and is aerosolized inside the cone closer to its apex, i.e. within the stem. The readily wettable/hydrophobic surfaces support this fluid flow. However, in the alternative, the lip does not need to be sharp, so that also a cone that does not occupy the entire diameter of the stem counts as a possible design.

According to another preferred embodiment of the nozzle of the invention, the cone-shaped gas exit channel subtends an angle between 15 and 80 degrees. The ideal cone shape varies with a number of different parameters, such as the speed of the flow, the size of the gap between annulus and stem, and the speed of the gas flow aerosolizing the fluid. A particularly advantageous angle for the cone is 45 degrees. Preferably, the base of the cone comprises a diameter between 1 and 2 mm and the nozzle gas supply channel comprises a diameter is between 0.05 mm and 1 mm.

According to another preferred embodiment of the nozzle holder of the invention, the nozzle body comprises a cylindrical nozzle body base having an outer cylindrical nozzle body base surface comprising an outer nozzle body base diameter, wherein an annular fluid supply channel is formed between the outer cylindrical nozzle body base surface and the cylindrical barrel hole wall. This transfers the fluid closer to the periphery of the barrel in an annular more peripheral channel to the front, while the gas flow is conducted in a centered channel. However, also other alternative designs for the fluid channel are possible, for instance longitudinal fluid channels running in parallel to the center of the barrel.

According to another preferred embodiment of the nozzle holder of the invention, the barrel comprises radial gas supply channels feeding gas to a central gas supply channel that is connected to the nozzle gas supply channel and comprises a diameter that is several times larger than that of the nozzle gas supply channel. This allows an effective radial gas supply, while the gas flows in parallel to the center channel of the barrel. However, also other designs of gas supply are possible, for instance an axial gas supply in a direction parallel to the fluid supply.

According to another preferred embodiment of the nozzle holder of the invention, the nozzle holder is designed as a disposable part that comprises in close proximity to the first end of the nozzle holder a knob for inserting and removing the nozzle holder into or from a receptacle of an aerosol generator. This allows to prepackage the inhalable medication and prevents misuse such as using the wrong dosage. However, in the alternative, also feeding the fluid containing the medication from a bulk container is possible, for instance for clinical use.

According to another preferred embodiment of the nozzle holder of the invention, the barrel comprises an outer cylindrical surface that is adapted to fit snugly into a receptacle of an aerosol generator. For this purpose, the barrel size can be size coded so that only a specific prepackaged nozzle holder fits into the receptacle. Specifically for home use, such a prepackaged design is very recommendable avoiding any misuse and unintended use of the wrong medication. Preferably, the nozzle holder and the fluid cartridge are pre-assembled as one disposable unit.

According to another preferred embodiment of the nozzle holder of the invention, the nozzle holder fluid inlet port is a Luer fitting that is adapted to receive a disposable fluid cartridge. However, any other fluid tight fitting works in the alternative.

Herein, this disclosure describes how a relatively high volume (up to 300 liters/minute) of low pressure aerosol is concentrated. The slits are arranged radially such that the exhaust gas is passively expelled radially between the slits. Such a design has many advantages:

a) The dilution gas is provided by a small (2 inch×2 inch×1 inch) gas blower or fan.
b) The device does not require tight high pressure seals thus enabling easy assembly and disassembly for cleaning and maintenance.
c) The exhaust gas requires no negative pressure source and is thus vented at atmospheric pressure.
d) The local counter-flow jet is structurally stable with precise reproducible coaxial alignment.
e) The localized heated jet and counter-flow gas together with the localized infrared radiation provide rapid drying of the aerosol leading to decreased wall losses and increased efficiency as well as enhancing the ability of the device to create particles with a density lower density than 1 gm/cc.

Devices which generate aerosols from liquids with refillable reservoirs have issues regarding the maintenance of their cleanliness. Devices which are used for multiple inhalations may have unpredictable or reduced output as the nozzle or orifices become clogged. This is especially a critical issue when large molecules such as proteins, surface active agents as well and other larger molecules are to be aerosolized. These issues are resolved in the present disclosure through the inclusion of replaceable or disposable cartridges with integrated single-pass nozzles.

In the aerosol generator of the present invention, for the purpose of describing the aerosol generator, the following assembly groups can be identified: the nozzle and nozzle-holder with its receptacle, the flow conditioner with its flow partitioners, the counter-flow tube and the evaporation chamber, the virtual impactor the eddy relaxation chamber and the aerosol delivery cone. These assembly groups interact with each other forming a portable compact device for the generation of concentrated dry aerosols from an aqueous (or high vapor pressure solvent) solution or suspension of the substance with the resultant aerosol being a dry concentrated aerosol comprised of the original solute or suspended material. Specifically, it relates to the methodology which demonstrates that this can be achieved in a practical compact portable device. Moreover, this device which enables extremely rapid evaporation of the solvent in close proximity to the base of the aerosol plume facilitates the generation of protein particles with a density of less than one.

An overriding design constraint throughout every aspect of the invention was to make the device fully operational using a dilution gas marginally above atmospheric pressure. This has two compelling advantages for a portable concentrated aerosol delivery system for patient use. Firstly, only a very small fan or blower with a limited pressure head is incorporated for size, weight and noise considerations. Secondly, the use of low pressure fittings enables easy assembly and disassembly for cleaning and maintenance.

Another design criterion was to provide heated compressed gas to a nozzle and a counter-flow jet so as to effect as rapid evaporation of the solvent as possible.

Another design criterion was to incorporate interchangeable removable nozzle-holder and nozzles. This increases the commercial flexibility and functionality of the device. This flow conditioner is compact and has a very low resistance to gas flow.

The features of this device include a) a compact two stage flow conditioner with an integral receptacle to accept exchangeable nozzle holders, b) a counter-flow compressed gas divider and counter-flow tube. c) gas heaters with low gas flow resistance and thermal inertia, d) proximal infrared radiation, e) Low resistance, high efficiency aerosol concentrator for particles>0.5 micron, f) a low resistance extracted gas filtering capability, and g) an aerodynamically designed collection "cone" to collect the concentrated output aerosol.

An instrument version of this device can be used to tailor the parameters of the aerosol drying process to the specific solute (suspension)/solvent solution to be delivered as a respirable aerosol. The invention can be used to deliver drugs without the need for the use of excipients that are most always required for re-aerosolization of the powdered drug. Biotherapeutics including proteins can be delivered directly to the patient. The particles so produced may have a particle density of less than one or a tap density less than 0.04.

Compressed gas is provided via a quick disconnect to a pressure regulator. The compressed gas from this regulator is passed though a heater and then to a port on the manifold of a flow-conditioner. Within the manifold the flow is redirected to two paths, a. to a nozzle-holder and thus to an aerosol generating nozzle and b. to a counter-flow tube whose exit port is aligned along the same axis as the nozzle. A source of low pressure gas at much high flows (100 to 300 liters per minute) is provided by a small blower. (Alternatively a compressed gas source could be used.) This gas is passed though a heater and then it enters through a port on the manifold of the two stage flow-conditioner. This flow-conditioner ensures a uniform flow in an adjoined Pyrex or quartz cylindrical evaporation chamber. The gas from the two stage flow-conditioner enters this evaporation chamber. Infrared radiation from an infrared lamp and reflector adjacent to this evaporation chamber is transmitted through the chamber and reflected by a second focusing reflector on the opposite side of the chamber. This evaporation chamber is connected to a virtual impactor aerosol concentrator. The gas enters through acceleration slit nozzles in an acceleration nozzle plate. A minor fraction of this gas which contains most of the particles exits the concentrator through collection deceleration nozzles in a virtual impaction plate. These deceleration nozzles are precisely aligned with the acceleration nozzles. The resulting aerosol from the deceleration nozzles loses much of its kinetic energy in the form of eddies in the relaxation chamber connected to the exit of the concentrator. From there, the aerosol flows through a tapered aerosol collection cone at the end of which the aerosol exits. The major fraction of the gas flow exits from the gaps between the acceleration nozzles and the deceleration nozzles in the acceleration nozzle plate and the deceleration nozzle plate, respectively. This exhaust gas then flows within a plenum to an optional filter to remove any remaining suspended particles in this exhaust gas.

Alternatively, for use where ample supplies of compressed gas are available, a quick disconnect for compressed gas is connected via a tee fitting to two pressure regulators, one for high pressure gas and the other for low pressure gas. The high pressure regulator is connected via a gas heater to the manifold of the two stage flow conditioner as described above. This compressed gas is redirected to two paths as noted above. The low pressure regulator is connected to a dilution gas heater and then to the flow-conditioner as noted above.

The compressed gas provides the energy for the aerosolization nozzle as well as for the counter-flow gas. The counter-flow gas flows coaxially and in the opposite direction to an aerosol plume formed by the nozzle such that the counter-flow gas arrests and dilutes the plume. The high pressure gas is heated, according to the desired use, up to 150° C. This temperature is regulated using the thermocouple in the compressed gas stream upstream from the heater using an associated Proportional-Integral-Derivative (PID) controller. This heated compressed gas is delivered to the flow-conditioner manifold via a quick disconnect. This flow is divided within the flow conditioning manifold. One flow goes through a small orifice and on to the counter-flow tube. The diameter of the small orifice determines the gas flow in the counter-flow tube. This flow is typically similar to or a little higher than the gas flow through the nozzle. The other gas flow goes to an annulus surrounding a cylindrical receptacle in the flow conditioner. Ports in a nozzle holder are aligned with this annulus and thus gas flows though the input ports of the nozzle holder though two conducting channels to a small pressure equalization chamber and to then to a nozzle. The fluid is delivered to the nozzle through a central channel. An external pump provides fluid flow rate between 0.1 and 5 ml/minute depending on the application. The aerosol is created by the interaction of the compressed gas with the fluid. The aerosol plume so created is arrested by a jet of gas from the counter-flow tube. The warm dilution gas from the flow-conditioner both enhances the evaporation of the liquid and transports the particles though the evaporation chamber towards the aerosol concentrator. Infrared radiation supplied by the infrared lamp and the corresponding reflector on the opposite side of the chamber augments the evaporation of the liquid from the particles. The particles are then concentrated as they pass through the virtual impactor and delivered via the output cone to the output. The output flow has a small positive pressure and is regulated by the apparatus or person connected to the output.

Alternatively, when ample supplies of high pressure as are available, the compressed gas enters the external quick-disconnect fitting and is split into two streams using the tee fitting. One goes to the high pressure regulator and the other to the low pressure regulator. Regulators rather than valves are used to control the gas flows and pressures downstream to these two regulators. This design enables excellent control of these rather diverse flows and pressures while minimizing any changes in these flows and pressures due to fluctuations in the upstream compressed gas pressure or adjustments made with the other regulator. In this preferred embodiment, the upstream pressures are generally between 30 and 100 psi. This does not exclude using higher or lower pressures. The low pressure regulator controls the downstream flow from 100 to 300 liters per minute.

To achieve optimal performance, the dilution gas as well as the compressed gas delivered to the nozzle and the counter-flow tube should be both dry and heated. As this device is planned for the respiratory delivery of pharmacologically active aerosols, it should be ready to use within one minute of turning it on. Thus, the temperature of the heated gas must rise to the operating temperature within one minute. This requires heaters with low thermal inertia and which exhibit a high transfer of energy from the heater to the gas flowing through it. Especially in the case of the dilution gas, this heater must offer minimal resistance to gas flow. This facilitates the use of a small gas blower. A heater with low gas flow resistance minimizes the size and pressure-head of the gas mover required.

In this disclosure radial slits with large length/width ratios are described to minimize end effects and provide a clear path for the exhaust gas to exit. The use of multiple slit lengths achieves two objectives, a) to maximize the total cumulative length of the slits to minimize the pressure drop across the concentrator and b) to achieve relatively uniform flow at the exit of the evaporation chamber as well as concentrically relatively uniform across the concentrator.

These and other advantages of one or more aspects of the invention will become apparent from the consideration of the ensuing description and accompanying drawings.

DETAILED DESCRIPTION OF THE DRAWINGS

Figure 1:
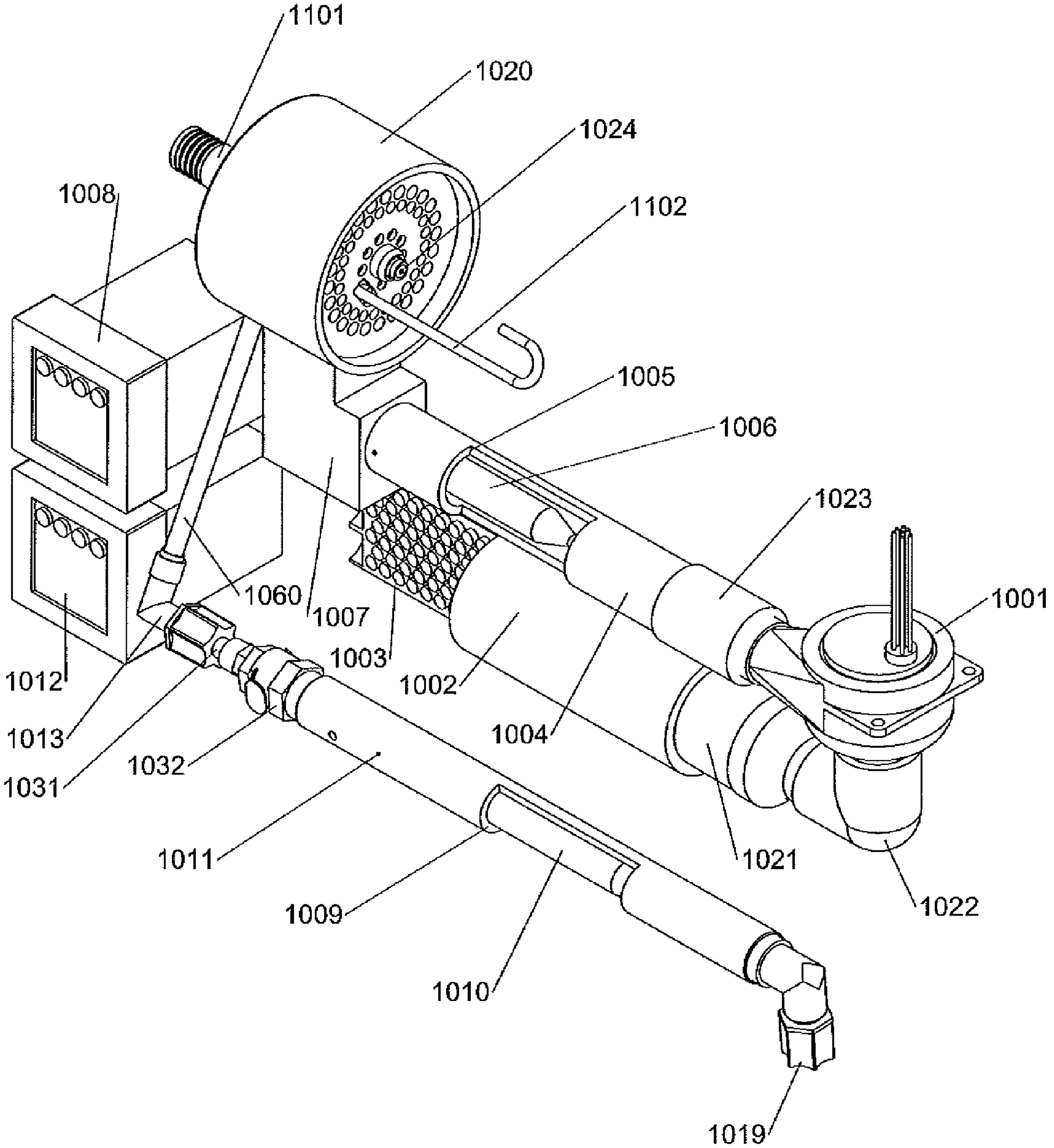
FIG. 1 shows a perspective view of the components for generating dry warm dilution gas and delivering it to the flow conditioner as well as the components for the heating and delivery of hot gas to the nozzle-holder and the counter-flow tube.

Referring to FIG. 1, for the purpose of describing the aerosol generator, the following assembly groups can be identified: a) the dilution gas drying chamber, blower and heater, b) the compressed gas heater c) the flow conditioner manifold and d) the counter-flow tube.

Input Gas Conditioning

Low pressure gas to dilute and evaporate the liquid aerosol travels through the flowing components. A gas dryer 1002 contains a desiccant 1003 such as, but not limited to, aluminum oxide pellets. This chamber 1002 is connected a gas filter 1021 and a fitting 1022 to a miniature blower 1001 or equivalent gas mover. The blower is connected via a flow measurement device 1023 to a dilution flow heater 1004. The flow measurement device may be a pneumotac, hot wire anemometer, mass flow meter or other low resistance device. The heater 1004 is comprised of a heat tolerant cylinder (1.0 inch OD 0.75 inch ID) 1005. In a preferred configuration, this cylinder is made of ceramic. Centrally located within the tube is a rapidly heating infrared bulb 1006. In a preferred configuration this rapidly responding infrared bulb 1006, has tapered ends to reduce gas flow resistance. This ceramic heating tube 1005 fits snugly in a fitting 1007 which has a right angled lumen. The other opening of fitting 1007 has a tapered receptacle (not shown). This enables easy placement a similarly tapered male fitting (not shown) on a flow conditioner manifold 1020. In a preferred configuration, the tapers on this port and receptacle are standard 22 mm respiratory tapers. There is an iron-constantan thermocouple (not shown) placed in the gas stream within the lumen of the right angle channel of the fitting 1007. This thermocouple is connected to a temperature regulating device 1008. In a preferred embodiment, the temperature regulating device is a PID controller which regulates the power supplied to the infrared bulb 1006.

High pressure gas to both generate an aerosol of the fluid in a cartridge 1101 with a nozzle 1024 and provide a co-axial counter-flow though counter-flow tube 1102 to arrest the aerosol plume comprises of the following components. The compressed gas enters a fitting 1019 and is warmed in heater 1011. In a preferred configuration, this heater comprises of a 0.75 inch OD 0.56 inch ID ceramic tube 1009 in which is placed an infrared bulb 1010. An iron-constantan thermocouple is located in the exit gas stream (not shown) on the female piece of a quick disconnect 1032 or other convenient location downstream from the heater 1011. This thermocouple is connected to a temperature regulating device such as a PID controller 1012. This quick disconnect is connected via a Teflon tube 1031 to a right angle fitting 1013. For illustration purposes a tube 1060 has been inserted to demonstrate the connectivity of the compressed gas flow to the inlet 4028 (see FIG. 4C) of the flow conditioner manifold 1020. Other configurations which achieve the desired functions are possible.

Input Gas Conditioning

Up to 300 liters of dilution gas is provided by the miniature blower 1001 or equivalent gas mover. When the relative humidity of the room gas is higher than desirable for the aerosolized volume of fluid to be dried, this dilution gas may be passed though the gas drying chamber 1002 containing the desiccant 1003. This dry gas passes through the filter 1021 to protect the blower from wear (due to any desiccant dust) via the fitting 1022 to the blower 1001. This dry gas is propelled by the blower 1001 through the flow meter or flow measuring device 1023 to the dilution flow heater 1004. The gas is heated in heater 1004 as it passes between the infrared bulb 1006 and the inside wall of the heat tolerant cylinder 1005 in the form of a ceramic tube. The temperature of the gas exiting the tube is measured with the iron-constantan thermocouple (not shown) placed directly in the gas-flow and the gas is maintained at the desired temperature, typically 35-45° C. using the temperature regulating device 1008 such as a PID controller which regulates the power supplied to the heater bulb 1006.

Similarly, the compressed gas, used for the nozzle and counter-flow gas is passed through the heater 1011. The gas is heated as it passes between the infrared heater 1010 and the walls of the ceramic tube 1009. The temperature of the gas exiting the tube is measured with the iron-constantan thermocouple (not shown) and maintained at the desired temperature typically 100-140° C. using the second PID controller 1012. This PID controller regulates the power in the infrared bulb 1010.

In another preferred configuration of this invention, compressed gas can be used as the source of dilution gas. In this case a pressure regulator would replace the dilution gas blower 1001. Compressed gas, or other gas, generally has had most, if not all, of its moisture removed. In this case an input high pressure fitting is connected via a high pressure tube and T piece to two gas pressure regulators (not shown). One regulator controls the gas flow to the compressed gas heater 1011 and the other controls the gas flow via the flow measuring device 1023 now placed between the regulator and the dilution flow heater 1004.

Replaceable Nozzle Holder and Nozzle

Figure 2A:
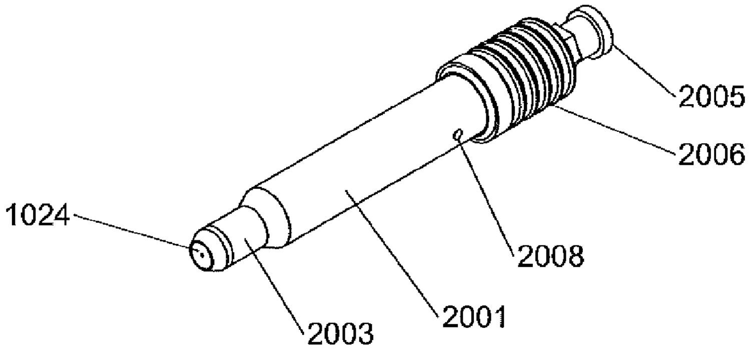
FIG. 2A shows a perspective view of a first embodiment of a nozzle-holder.
Figure 2B:
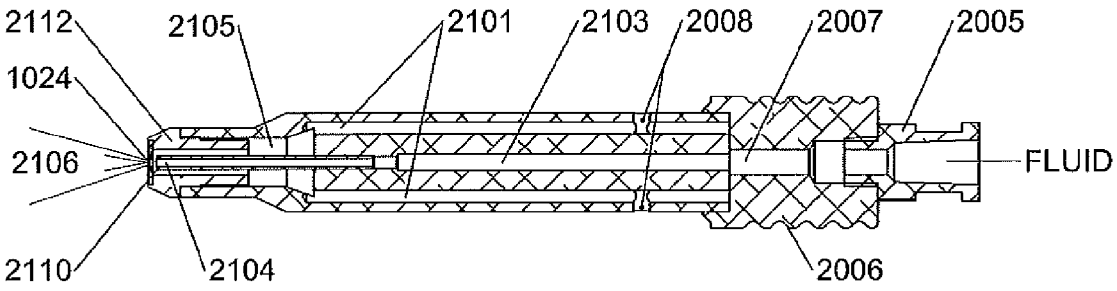
FIG. 2B shows a longitudinal section of the nozzle-holder shown in FIG. 2A.
Figure 2C:
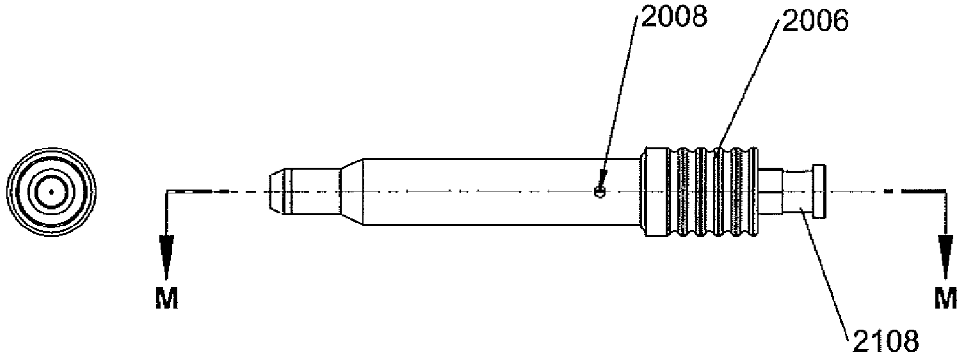
FIG. 2C shows a side view of the nozzle holder shown in FIG. 2A.

A schematic figure showing the features of a preferred configuration of a nozzle-holder is shown in FIG. 2A to FIG. 2C. The nozzle holder is comprised of an aerosol generating nozzle 1024 mounted with in a fitting 2112 on a neck 2003 at the end of a barrel 2001. A narrowing from the barrel to the neck 2003 enables gas to streamline along the neck adjacent to the nozzle. This minimizes any deposition of particles on the face of the nozzle through eddy currents that would be induced by a large flat surface near the nozzle. The nozzle 1024 in FIG. 2B is contiguous with a small pressure equalization chamber 2105 which in turn is connected to two channels which terminate at one or more ports 2008. A tube 2104 in close proximity to the nozzle and coaxial with the nozzle orifice is connected to another channel 2103 and 2007 to a connector 2005. At the other end of the barrel is a knob 2006 with several circumferential grooves to permit easy insertion and withdrawal of the nozzle holder into a receptacle (see 4030 FIG. 4A and FIG. 4C) within the flow conditioner manifold 1020. The connector 2005 at the opposite end to the nozzle enables the attachment a fluid line (not shown). In a preferred configuration this is a Luer connector. Ports 2008 in the barrel 2001 interface with compressed gas supply groove (see 4071 FIG. 4C) in the flow-conditioning manifold 1020. According to the invention, these nozzle holders must be inserted into the flow conditioner. This feature essentially eliminates the indiscriminant use of this nozzle holder by a patient. This protects the patient and helps ensure the proper delivery of the contents of the cartridge.

In one preferred nozzle-holder configuration FIGS. 2A, 2B, 2C and 2D the nozzle 1024 requires both high pressure gas and high pressure fluid to generate a satisfactory aerosol. The connector 2005 having a fluid port is connected via a channel 2007 to the channel 2103 and to a tube 2104. In a preferred configuration, this tube 2104 has and internal diameter of 0.03 inches and it has a port 2110 that is positioned one to 1-2 diameters from a 0.014 in diameter orifice in the nozzle 1024. These dimensions are not provided to exclude other diameters and distances but rather as working examples. The nozzle 1024 is contained within in the fitting 2112 to ensure that the orifice and the tube 2104 are precisely coaxial. This design is provided as an example. Similar configurations can be achieved with other designs. The compressed gas intake ports 2008 are on the side of the barrel 2001 of the nozzle holder. The ports 2008 are connected to one or more channels 2101 to the pressure distribution chamber 2105. This chamber 2105 extends into the nozzle body to facilitate even gas flow around the tube 2104 to the orifice in the nozzle. A liquid aerosol plume 2106 is formed at the exit of the nozzle 1024. The knob, 2006 acts as a stop to limit the distance that the barrel 2001 is inserted into the receptacle 4030 FIG. 4A and FIG. 4C in the flow conditioner manifold 1020. The circumferential grooves on knob 2006 facilitate easy insertion of the nozzle holder into the barrel of the flow conditioner and well as its removal from the flow conditioner.

In this configuration of the nozzle-holder, fluid is supplied by an external pump (not shown) through the connector 2005 on the nozzle holder. The fluid stream flows through the channel 2007 and through the center channel 2103 along the center of the nozzle barrel 2001. The tube 2104 transports this fluid to its port 2110. Compressed gas enters through the ports 2008 on either side of the barrel 2001. This compressed gas enters channel(s) 2101 on either side of the central channel 2103. These outer channels transport the compressed gas to the pressure equalization chamber 2105. The compressed gas in the chamber 2105 flows around the tube 2104 causing the fluid to flow through the center of the orifice of the nozzle 1024 without the fluid coming in contact with the orifice. The aerosol is created by focusing the flow of this fluid through this nozzle 1024. At the down-stream side of the orifice, the liquid aerosol plume 2106 is formed.

Figure 2D:
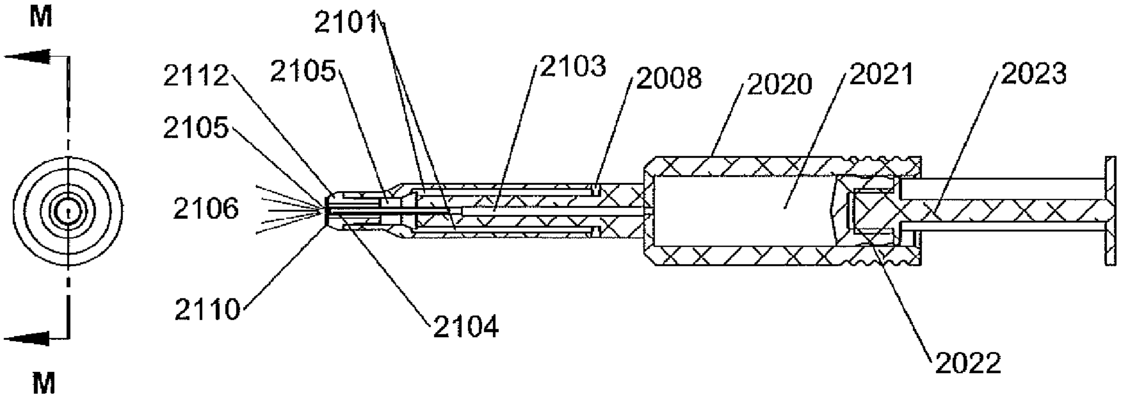
FIG. 2D shows a longitudinal section of a second embodiment of a nozzle holder where the knob on the nozzle holder illustrated in FIGS. 2A, 2B and 2C is replaced with a cartridge containing the liquid to be aerosolized.
Figures 3A, 3B, 3C, 3D, 3E, 3F:
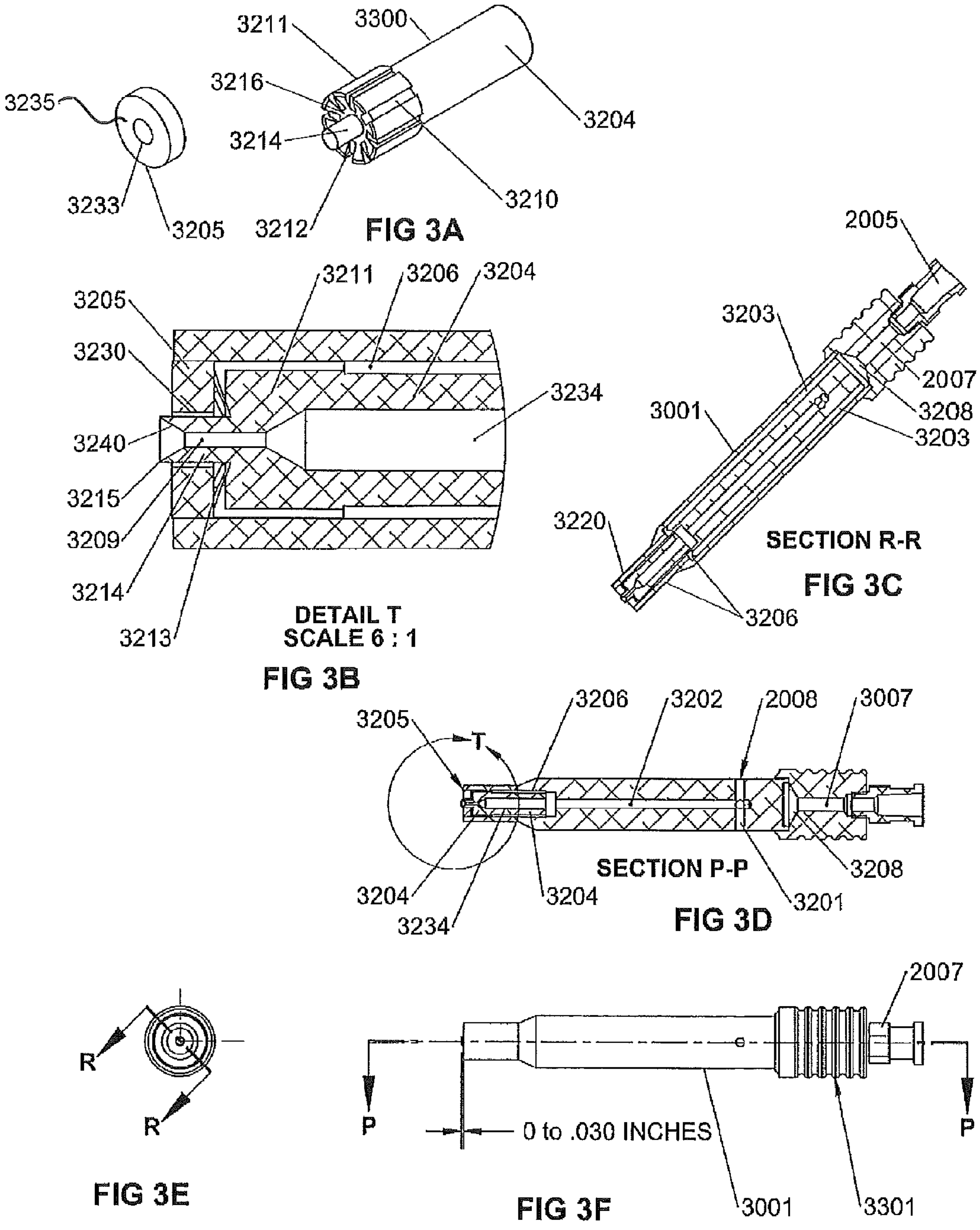
FIG. 3A shows an exploded perspective view of a nozzle body and annulus which fits over the stem protruding from the nozzle body.
FIG. 3B shows a partial longitudinal section denoted T in FIG. 3D of the nozzle within a neck section of the barrel of the nozzle holder.
FIG. 3C shows a longitudinal section denoted R-R in FIG. 3E of the nozzle holder.
FIG. 3D shows a longitudinal section of the nozzle holder at a 90 degree rotation compared to FIG. 3C and in line with the side view illustrated in FIG. 3F where this longitudinal section is denoted P-P.
FIG. 3E shows a front end view of the nozzle and barrel and illustrates the section R-R shown in FIG. 3C.
FIG. 3F shows a side view of the nozzle holder illustrating the section P-P shown in FIG. 3D.

In another preferred configuration FIG. 2D, a cylindrical cartridge 2020 is incorporated into the nozzle holder in place of the knob 2006 and connector 2005 shown in FIGS. 2A, 2B and 2C. The fluid to be aerosolized is contained within a chamber 2021 in this cartridge 2020. The chamber 2021 of this cartridge has a piston 2022 which can be translated down the inside of chamber. This chamber is connected to the channel 2103. This piston 2202 can be depressed with a plunger 2023 attached so it can be used multiple times or it can be depressed using a rod that is not attached to the piston such that it can be a single use nozzle system. The plunger or rod can be depressed with a servomotor or other means. Several circumferential grooves around the cartridge 2020 facilitate the easy insertion into, and removal of this cartridge-nozzle holder from the receptacle 4030 (see FIG. 4A and FIG. 4C) of the flow conditioner 1020.

Alternative Nozzle-Holder and Nozzle

FIGS. 3A, 3B, 3C, 3E, 3F show a nozzle and nozzle-holder which uses high pressure gas in the center of a low pressure fluid flow. This second nozzle and nozzle holder are used as an illustration of the breadth of the utility of the design of the receptacle 4030 (see FIG. 4) within the flow conditioner manifold 1020 to incorporate nozzles with quite different operational functionality. This alternative nozzle-holder has external features and functionality in common although its configuration and nature of aerosol generation are quite different. These nozzles are both single pass nozzles, i.e. all the liquid is aerosolized on passage through the nozzle. None of this fluid is recirculated. Both nozzles, however, share the distinction that the aerosol is generated through the shear forces between the liquid and the gas. In neither case is the aerosol generated through the shear of the liquid on a solid. This reduces the possibility of high shear forces causing shear degradation of any large molecules dissolved in, or suspended in, the fluid to be aerosolized.

In this alternate preferred configuration, the nozzle-holder and the nozzle are shown in FIGS. 3A, 3B, 3C, 3D, 3E and 3F. As noted, this configuration enables the aerosol is generated using compressed gas though a central channel together with a low pressure fluid flow to the perimeter of the compressed gas nozzle. The connector 2005 (see FIG. 3C) is situated on the end of the nozzle holder. In a preferred configuration of the invention, this connector 2005 is a Luer fitting. This connector 2005 is connected via channel 2007 and a small distributive reservoir 3208 to one or more channels 3203 (see FIG. 3C) and so to an annular cavity 3206 surrounding a base 3204 of the nozzle body 3300 (see FIG. 3A). In this case, the nozzle is comprised of two components, a nozzle body 3300 and a nozzle annulus 3205. The nozzle body 3300 is seated within a neck 3220 of the nozzle barrel 3001 (see FIG. 3C) with the base 3204 of the nozzle body sealed to the barrel of the nozzle holder. The annular cavity 3206 (see FIG. 3B) is connected via grooves, e.g. grooves 3210 (see FIG. 3A) and 3212 in a crown 3211 of the nozzle body 3300 to a miniature reservoir 3213 (see FIG. 3B) formed between a concave indentation 3216 in the crown 3211 and the annulus 3205 seated atop of the crown 3211. This reservoir 3213 is contiguous with an annular cavity 3230 between a stem 3214 on the nozzle body 3300 and the annulus 3205. The annulus 3205 is seated within and at the end of a neck 3220 of the nozzle barrel 3001 (see FIGS. 3C and 3D) such that a central hole 3233 in the annulus 3205 is positioned concentrically around the stem 3214 (see FIG. 3B). The distance between the stem and the annulus is small enough such that surface tension rather than gravity dominates the movement of fluid. The diameter difference between the inner annulus diameter and the stem diameter is between 0.006 and 0.8 mm, resulting in an annular gap width between the 0.003 and 0.4 mm. The stem 3214 which is in a preferred configuration is 1.75 mm but may vary from 0.5 mm to 3 mm has an orifice 3209 which in a preferred configuration is about 0.5 mm in diameter although other nozzle dimensions from 0.05 to 1 mm may be used. The orifice exits at the apex of a hollow cone 3240 within the stem 3214. A lip 3215 on the cone 3240 is either level with the front face 3235 of the annulus 3205 or protrudes slightly from this front face 3235, potentially up to 1 mm. The nozzle body 3300 is comprised of machined ceramic or other material which is wettable by the solution or suspension to be aerosolized. In the case of an aqueous based solution, the nozzle should have a high surface energy to improve wettability. This may be achieved by applying a hydrophilic agent or other means. The outer surface of the annulus 3205 is coated with a hydrophobic agent to prevent an aqueous fluid from spreading across this annulus. The nozzle barrel 3001 of the nozzle holder has one or more ports 2008 which are connected via a radial channel 3201 to a channel 3202 (see FIG. 3D). The channel 3202 in turn is contiguous with a channel 3234 of similar diameter within the nozzle body 3300. This is contiguous with the orifice channel 3209. In a preferred configuration, the nozzle barrel 3001 and a knob 3301 (see FIG. 3F) are constructed of either polysulphone or ultem although other materials may be used.

Generating an Aerosol by the Nozzle-Holder and Nozzle Shown in FIGS. 3A-F

In this preferred configuration of the nozzle-holder shown in FIGS. 3A, 3B, 3C, 3D, 3E, and 3F the aerosol is generated by supplying compressed gas to the central orifice 3209 within the nozzle. The fluid to be aerosolized is fed at a low pressure through the annular cavity 3206, reservoir 3213 and the annular channel 3230 to the outer surface of the nozzle and by capillary action within the cone 3240 towards the orifice 3209. The fluid to be aerosolized is supplied to connector 2005 by an external pump (not shown). The fluid is pumped into the connector 2005 and into channels 3203 to the annular space 3206 surrounding a base of the orifice body 3124. This fluid distributes itself to each of the grooves 3210 in the side of the crown 3211 of the nozzle and through the grooves 3212 to the miniature reservoir 3213. The top of the crown is concave to ensure the fluid is presented uniformly to the cavity 3230 surrounding the stem 3214. The fluid flows evenly through the space 3230 between the stem and the annulus to the lip 3215 of the nozzle. In a preferred configuration, the stem 3214 may protrude some 0 to 0.050 inches through the annulus. The fluid flows over this lip 3215 to form a thin film on the inner surface of the cone 3240 within the stem 3214. The compressed gas enters through the ports 2008 in the side of the nozzle barrel 2001. The gas flows through the central coaxial channel 3202 to the channel 3234 along the axis of the nozzle body 3300. The compressed gas then goes through the orifice 3209. Aerosolization occurs at the junction formed by interaction of the fluid flowing into the cone and the gas jet at the perimeter of the orifice 3209 at the apex of the cone 3240. In this way large shear stressed between any solid surface and the fluid are avoided. A plume of aerosol is generated which has particle free center. The negative pressure within the cone caused by the gas jet aids in the formation of a thin fluid film on the inner surface of the cone. For optimal function the cone apex should subtend a solid angle of about 45 and preferably between 15 and 80 degrees. However, other angles between 10 and 80 degrees may be possible. It is noted that all the surface through or over which the fluid is designed to flow should have high surface energies, i.e. be wettable by the fluid. The fluid flows over the lip of the cone by capillary forces. These forces increase as the fluid flows into and towards the apex of the cone. As noted, the maintenance of this thin fluid layer is also aided by the negative pressure created by the jet of gas exiting the orifice 3209.

For optimal function, it is important that the surfaces of the nozzle body, including the crown and stem as well as the internal surface of the annulus have a high surface energy such that they are readily wettable by an aqueous based fluid. On the other hand, the top surface of the annulus 3205 has a hydrophobic coating to stop any fluid flow across the annulus. The distance between the stem and the annulus is small enough, for instance ~0.17 mm such that surface tension rather than gravity dominates the movement of fluid. As the stem has a high surface energy, the fluid forms a meniscus between the lip 3215 of the cone 3240 on the stem 3214 of the nozzle and the annulus.

Positioning of the Nozzle Holder for Insertion into the Flow Conditioner

Figure 4A:
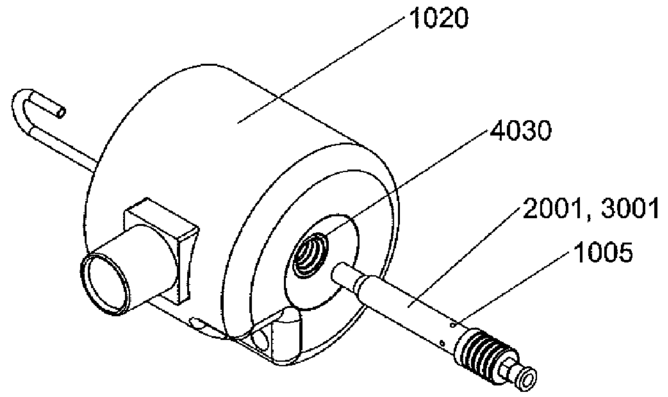
FIG. 4A shows an exploded perspective view of a flow conditioner manifold and a nozzle holder and the relationship between this nozzle holder and its insertion into the manifold of the flow-conditioner.
Figure 4B:
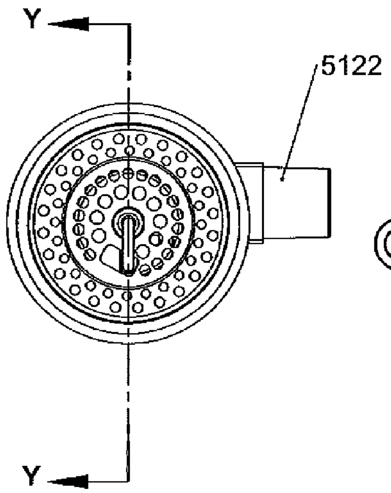
FIG. 4B shows a front view of a flow conditioner and illustrates the section shown in FIG. 4C.
Figure 4C:
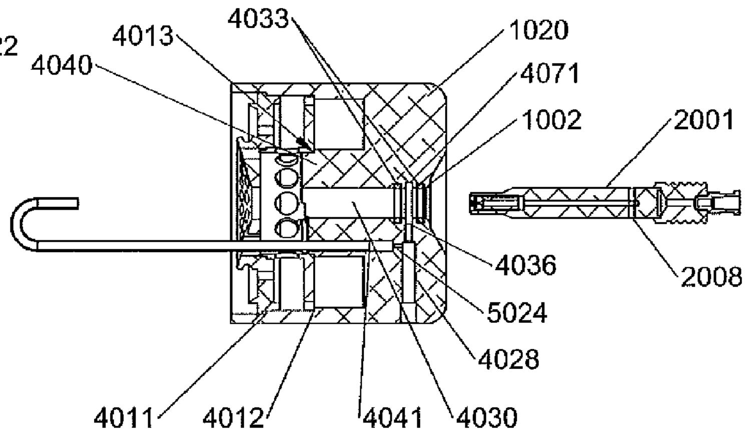
FIG. 4C shows an exploded longitudinal section denoted Y-Y in FIG. 4B of the flow conditioner as illustrated in FIG. 4B as well as the section of the nozzle holder at the opening of a receptacle to which it is inserted.

The positioning of the nozzle holder for insertion into the flow conditioner is shown in FIGS. 4A, 4B and 4C. The nozzle holder is aligned with a central axial receptacle 4030 in the flow conditioner manifold 1020 (See FIG. 4A and FIG. 4C). The barrel 2001 or 3001 of the nozzle holder is inserted in this receptacle 4030 of the flow-conditioner 1020. When the nozzle holder is fully inserted, ports 2008 for the compressed gas, used for aerosolization, align with the circular groove 4071 in the flow conditioner 1020. There is an O-ring 4033 on each side of this groove to prevent leakage of the compressed gas from the groove 4071. The compressed gas enters the circular groove 4071 through a channel 4036 which in turn is connected to a compressed gas input 4028. In the center of the manifold is a pillar 4040. This pillar 4040 facilitates the inclusion of the receptacle 4030 which has a 4:1 length to width ratio. This ensures both a snug positioning of the nozzle barrel 2001 or 3001 and its precise axial alignment. This is important as the aerosol plume must be precisely aligned with the axis of the counter-flow gas for efficient performance.

Flow Conditioner Design

Figure 5B:
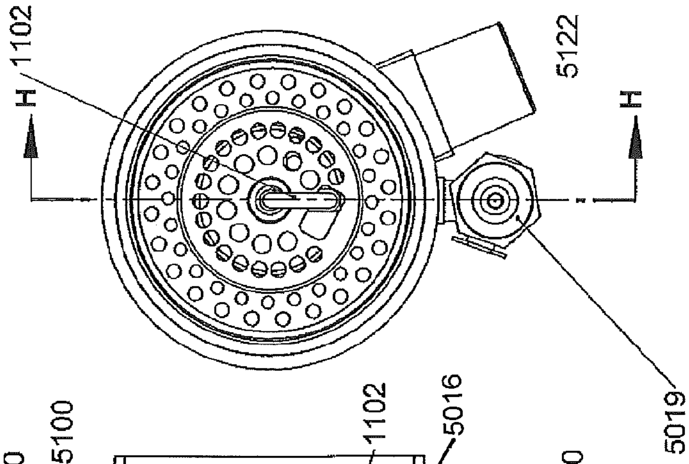
FIG. 5B shows a front view of the flow conditioner shown in FIG. 5A and illustrates the section of the flow conditioner shown in FIG. 5A.
Figure 5A:
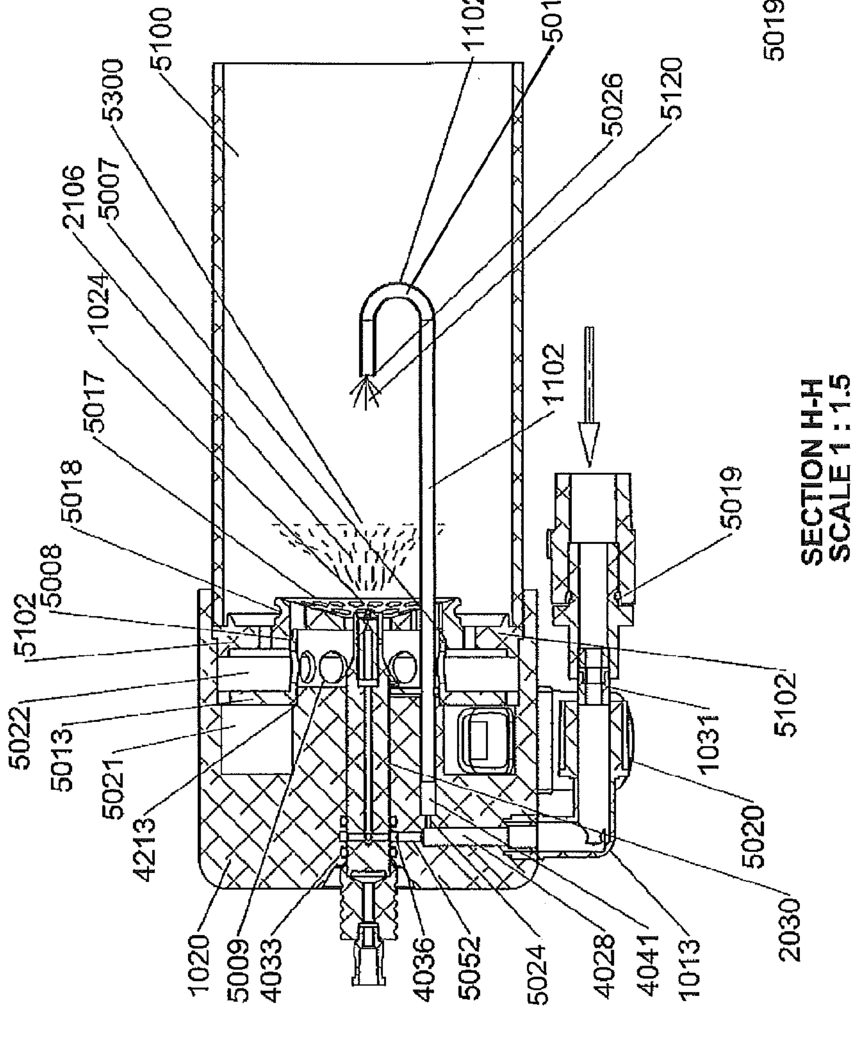
FIG. 5A shows a longitudinal section of the flow conditioning manifold and flow partitioners as indicated as section H-H in FIG. 5B as well as the relationship between the flow conditioning manifold and walls of the evaporation chamber. The compressed gas flow path to the nozzle holder and counter-flow tube is indicated.

Exploded and cross-sectional views showing the individual components which comprise the flow conditioner which affects the flow profiles of the dilution gas flow are shown in FIGS. 5A, 5B, 5C, 5D, 5E and 5F. In FIG. 5A an adjoining evaporation chamber 5100 is also denoted. To augment the rapid evaporation of the liquid aerosol in a confined space, the aerosol plume formed by either one of the nozzles described must be rapidly dispersed and diluted while providing sufficient thermal energy to evaporate the liquid. The flow conditioner must provide a uniform flow of gas through the evaporation chamber 5100 while again having a minimal pressure drop. This is made more challenging by the presence of the aerosol plume 2106 (See FIG. 5A) and the jet of gas 5120 (see FIG. 5D) from a counter-flow tube 1102. As noted, this must be achieved with minimal pressure drop across flow conditioner to minimize the power and size of the fan required. A small compact flow-conditioner which is inexpensive to manufacture and is easy to assemble and disassemble for cleaning clearly makes the end product more commercially attractive. The flow partitioners are designed to reduce the radial velocity of the incoming dilution gas and to distribute the gas such that at the exit of the evaporation chamber the gas has a near uniform velocity. These components of the flow conditioner are constructed for easy assembly and disassembly while maintaining full functionality.

Figure 5C:
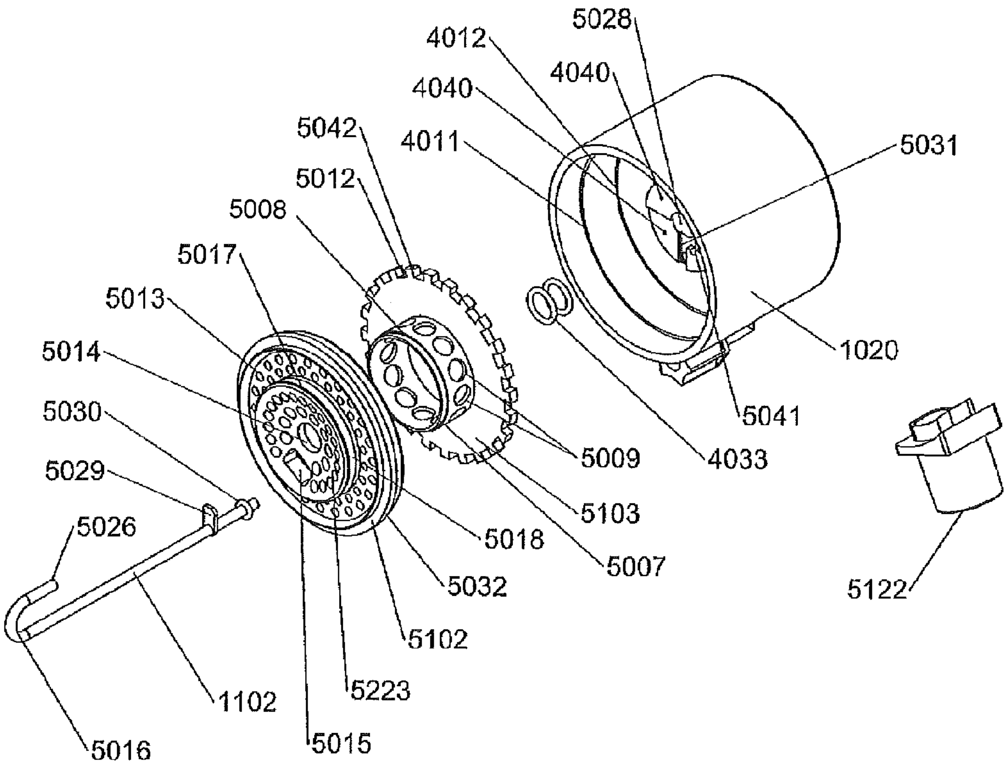
FIG. 5C shows an exploded perspective view of the flow conditioner. It shows the details of the flow conditioner and the counter-flow tube.
Figure 5D:
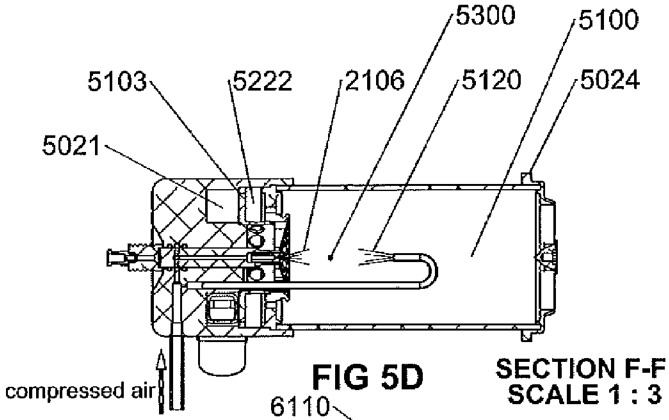
FIG. 5D shows a cross longitudinal section denoted F-F in FIG. 5E of the flow conditioner together with the evaporation chamber and the acceleration plate of a virtual impactor aerosol concentrator and the interrelationships between these components of the device.
Figure 5E:
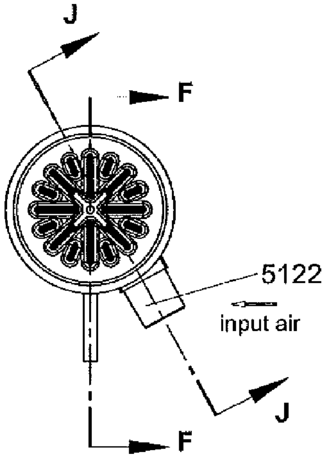
FIG. 5E shows a sectional view of the concentrator illustrating the longitudinal sectional views of the flow conditioner, evaporation chamber and acceleration plate of the concentrator shown in FIGS. 5D and 5F.
Figure 5F:
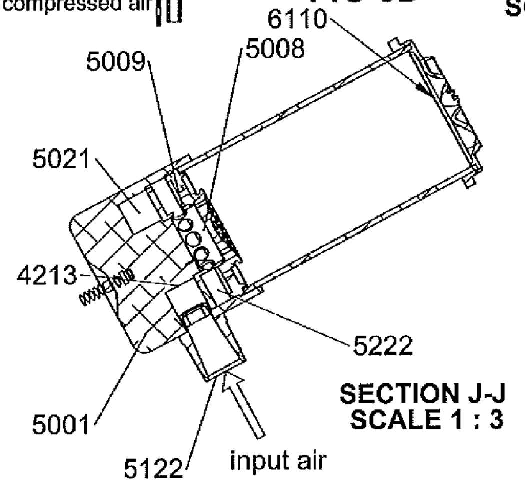
FIG. 5F shows a longitudinal section denoted J-J in FIG. 5E of the flow conditioner, evaporation chamber and acceleration plate of the concentrator as indicated in FIG. 5E. The relationship of the input dilution gas port to the first pressure equalization chamber of the flow conditioner is also shown.
Figure 6A:
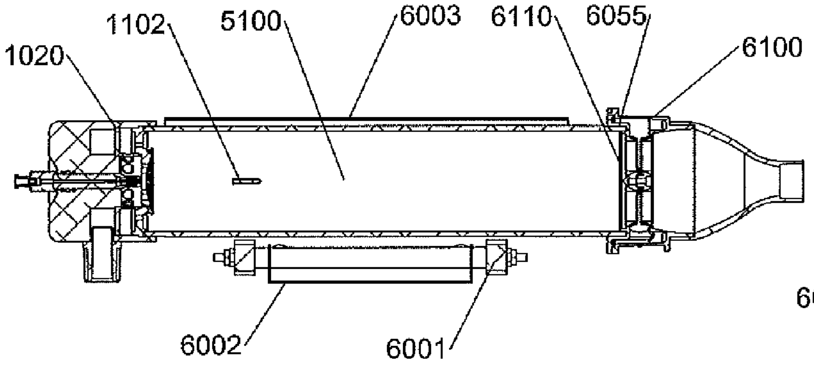
FIG. 6A shows a longitudinal section denoted J-J in FIG. 6B of the flow conditioner, evaporation chamber, concentration, output cone, infrared lamp and the reflectors as depicted in FIG. 6B showing the interrelationships between each of these components.
Figure 6B:
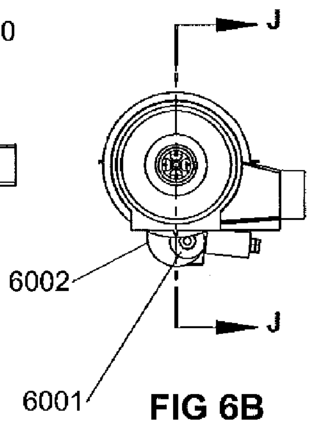
FIG. 6B shows a rear view of the flow conditioner, evaporation chamber, concentration, output cone, infrared lamp and the reflectors as shown in FIG. 6A.
Figure 6C:
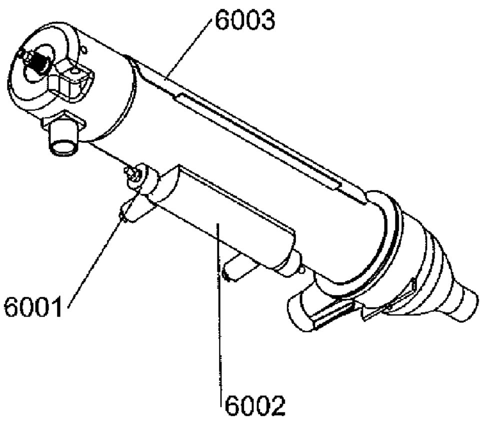
FIG. 6C shows a perspective bottom view of the components enumerated in FIG. 6A illustrating their positions in relation to each other.
Figure 6D:
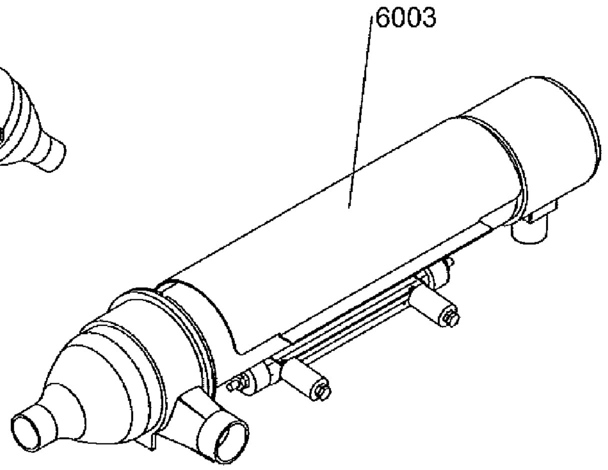
FIG. 6D shows a perspective top view of the components enumerated in FIG. 6A illustrating their positions in relation to each other.

The exploded rendition of the components used to transform a relatively high velocity dilution gas flow entering a port 5122 (see FIG. 5B) to a lower velocity gas flow that is relatively uniform at the exit of an evaporation chamber 5100 is shown detail in FIG. 5C. A cross-section of the assembled parts together with a head-on view of the flow conditioner indicating the location of the port 5122 for the dilution gas and port 4028 for the compressed gas is contained in FIGS. 5A and 5B. The flow conditioner consists of four primary components: a manifold 1020, two flow partitioners 5102, 5103, and a counter-flow tube 1102. As shown in FIG. 4A and FIG. 4C the manifold 1020 has the input for compressed gas 4028, the input for dilution gas 5122, the receptacle 4030 into which the nozzle holder is inserted, the central stabilization pillar 4040, a receptacle for a counter-flow tube 4041 and two circumferential steps 4011, and 4012 as well a step 4013 on the end of the pillar 4040. These steps facilitate the firm localization of the two flow partitioners 5103 and 5102 (see FIG. 5C). Of course these two flow partitioners 5103 and 5102 could be manufactured integrally as one piece. The manifold 1020 of the flow-conditioner is comprised of Ultem or other strong heat resistant non-conductive material, with excellent dimensional stability; as are the two flow partitioners 5102 and 5103. The flow partitioners remain in place as shown in FIG. 5 during normal operation and handling. They are easy to remove and replace. This functionality is achieved through specific design features subsequently described. The entry port on the flow conditioner for dilution gas 5122 is made with a 22 mm standard respiratory male taper. This port fits into the corresponding female taper (not shown) in fitting 1007 (see FIG. 1). Thus, the flow conditioner is held snugly in position by gravity.

The port 4028 for compressed gas is located within the flow conditioning manifold 1020. The compressed gas flowing through this port is divided into two. One flow is directed though the channel 4036 to the annular groove 4071 within the central receptacle 4030. There are O-rings 4033 in grooves on either side of the annular groove 4071 in the central coaxial receptacle 4030. The flow divider is also connected to a restriction 5024 which in turn in connected via the counter-flow receptacle 4041 to the counter-flow tube 1102.

The counter-flow tube 1102 has a 180 degree bend 5016 which reverses the direction of gas flow and directs it towards the oncoming aerosol plume 2106 generated by the nozzle 1024. The counter-flow has a small plate 5029 attached to the side which, when inserted into the flow conditioner interacts with a slot 5031 in the pillar 4040 of the flow conditioner such that when the counter-flow tube is seated, the counter-flow tube is precisely coaxial with the nozzle 1024. In a preferred configuration, the counter-flow tube is comprised of 12 gauge stainless steel tubing. In a preferred configuration, outlet of the counter-flow tube is 2 inches from the nozzle 1024. This does not exclude other combinations of tube diameters and nozzle to counter-flow distances but rather forms an example.

The two flow partitioners 5102 and 5103 are designed to reduce the radial velocity of the incoming dilution gas and to distribute the gas such that at the exit of the evaporation chamber 5100 has a near uniform velocity. These components of the flow conditioner are constructed for easy assembly and disassembly while maintaining full functionality. These two flow partitioners 5102 and 5103 divide the chamber of the manifold 1020 into two pressure/flow equalization chambers, 5021 and 5222. The flow partitioner 5102 is of slightly larger diameter than the circumference of flow partitioner 5103. The flow partitioner 5103 has a "chimney" 5008 with circumferentially placed holes 5009. The top of the chimney has a circumferential ledge 5007 which provides a means of stabilization for the second flow conditioner. Flow partitioner 5103 is inserted into the chamber of the flow-conditioning manifold such that it seats on the stepped circumferential step 4012 on the inside of the flow conditioner as well as the circumferential step 4013 on the central pillar 4040 of the manifold 1020. The flow partitioner 5102 is inserted into the chamber of the flow manifold 1020 such that the flow partitioner seats on the step 4011 in the manifold.

Of note, there are four surfaces of contact between the flow conditioner manifold 1020 and the first flow partitioner 5103 (see FIG. 4C and FIG. 5A). It is these surfaces that provide stable seating of the flow partitioner within the housing. Again, these multiple surface contacts facilitate the easy seating of this second flow conditioner yet secure it in place so that it does not fall out or move during normal handling and operation of the device. Also it is notable that through the use of these multiple steps, the gas flow is directed though holes 5013, 5023 and slots 5012 in the flow partitioners 5102 and 5103 (see FIG. 5C) rather than "leak" through the contact areas between the flow partitioners and the manifold 1020. In this way, the flow is controlled by the size of the flow channels rather than leaks. The use of O-rings is avoided. The use of such large O-rings would make the parts too difficult to assemble by a patient or end user. This minimizes aerosol deposition on this flow partitioner. The flow partitioner 5102 has a central hole 5014 through which the nozzle neck 2003 protrudes. It has a near rectangular hole 5015 to facilitate the insertion of the counter-flow tube 1102. A central part 5017 of the flow partitioner 5102 is raised. This facilitates the inclusion of a circumferential groove 5018. This groove enables a user to grip the outer flow partitioner with their fingers for easy removal and insertion to and from the flow-conditioner manifold 1020. The raised center of the flow conditioner has a concave surface to reduce aerosol deposition on its surface.

The flow conditioning manifold performs multiple functions central to the successful operation of the device. These include a) the locating of the nozzle holder precisely on the central axis of the receptacle of the manifold; b) the delivery and partitioning of compressed gas to the inlet ports 2008 (see FIG. 2B) on the barrel 2001 of the nozzle holder as well as to the counter-flow tube 1102 (see FIG. 4C) and c) the intake and redistribution of dilution gas to achieve near uniform gas flow at the exit of the evaporation chamber 5100 (see FIG. 5A).

Partitioning of the Compressed Gas

In FIG. 5A it can be seen that the compressed gas is connected via a quick-disconnect fitting 5019 and the Teflon tube 1031 through the right angle fitting 1013 on the manifold of the flow conditioner 1020. To simplify the practicality and use of the device, there is only one connector on the flow-conditioning manifold for the compressed gas 4028. The compressed gas flow is partitioned using an internally located flow divider within the flow conditioner manifold. One flow is directed to an annular groove through the channel 4036 to the annular groove 4071 within the central receptacle that provides the compressed gas to the nozzle holder. O-rings 4033 in grooves on either side of the annular groove 4071 in the central receptacle 4030 seal against leakage of the compressed gas. The other flow passes through a restriction 5024 which limits the flow rate of the counter-flow gas at a similar or slightly larger volumetric flow rate as that coming through the aerosolization nozzle 1024. The liquid aerosol plume 2106 is arrested by the co-axial counter-flow jet of gas 5120 from a port 5026 of the counter-flow tube 1102 such that a stagnation point 5300 is midway between the nozzle and the counter-flow port 5026 (see FIG. 5A).

Functions Performed by the Dilution Gas Flow Conditioner

The input gas flow from the entry port 5122 (see FIG. 5B) is directed circumferentially is the pressure equalization channel 5021 around the center pillar 4040 (see FIG. 4C) of the first stage of the flow-conditioner. This first stage is a hollow "donut" of low gas flow resistance. The rotational velocity of the gas is reduced as it moves perpendicularly through the slots 5012 (see FIG. 5C) located circumferentially between the merlons 5042 on the flow partitioner 5103. These slots form a gas flow path of higher resistance than that of the channel forming this first donut-shaped pressure equalization chamber 5021. The gas enters the second stage of the flow conditioner through these slots 5012, into a second donut-shaped pressure equalization channel 5022 with low flow resistance. From this channel, it is distributed in two ways; a) through holes 5009 around a ‘chimney’ 5008 and subsequently through holes 5223 in the center portion of the second flow-partitioner and b) through the concentric holes 5013 in the outer region of the second flow partitioner 5102. The positions and sizes of these holes (or slits) achieve a uniform flow profile at the virtual impactor face plate while minimizing deposition of aerosol on the second flow partitioner 5103 and the walls of evaporation chamber 5100. The gas flow to the center of the evaporation chamber in-part is regulated by the size of the holes 5009 in this ‘chimney’.

The Evaporation Chamber

The features of the evaporation chamber 5100 see FIG. 5A are shown in FIGS. 6A, 6B, 6C and 6D. The evaporation chamber 5100 fits between the flow conditioning manifold 1020 and an aerosol concentrator 6100. In a preferred configuration the evaporation chamber is comprised of a 2.75 inch outer diameter 2.56 inch internal diameter tube 6 inches long that is transparent to infrared radiation. Other similar dimensions are possible. In preferred configurations, this tube can be made of quartz or borosilicate glass. This tube is inserted into the open end of the flow-conditioner manifold 1020 until it abuts the flow partitioner 5102 (see FIG. 5A). The dimensions of the manifold opening and the tube are such that a friction fit is sufficient to a) support the tube and b) prevent any substantial gas leak from the inside of the chamber to the atmosphere. The other end of evaporation chamber is inserted into a circumferential groove 6055 (see FIG. 6A and FIG. 7C) on an acceleration plate 6110 (see FIG. 6A) of the virtual impactor type aerosol concentrator 6100. Again this is a snug friction fit. Alternatively, lip seals or tapered ends of this tube-shaped evaporation chamber 5100 and corresponding female tapers on the manifold 1020 and the concentrator acceleration plate 6110 could be used to eliminate any gas leakage between the evaporation chamber 5100 and the flow conditioner manifold or the aerosol concentrator 6100, respectively.

On one side of and adjacent to the evaporation chamber is a 125 W rapidly heating infrared lamp 6001. A preferably parabolic infrared reflector 6002 is placed behind the bulb such that the center of the bulb is in the focal plane of the reflector. In addition an infrared reflector 6003 on the opposite side of the evaporation chamber 5100 again increases the infrared radiation flux within the evaporation chamber. In a preferred configuration these infrared reflectors are made of polished aluminum. The infrared reflector 6003 may also be comprised of a gold coating on the evaporation tube. Also the reflector 6002 may be replaced with gold coating on the infrared lamp 6001.

To augment the rate of evaporation, the aerosol flowing through the evaporation chamber 5100 is heated with infrared radiation. Heat transfer by convection is proportional to the temperature gradient. However, heat transfer by radiant heat is proportional to the fourth power of the temperature differential. Water has strong absorption bands in the infrared region. Thus, the rapidly responding infrared lamp 6001 is located below the evaporation chamber 5100. The infrared reflector 6002 increases the infrared radiation flux within the evaporation chamber 5100. The quartz or borosilicate glass of the evaporation chamber, being transparent to infrared enables the infrared radiation to enter the evaporation chamber 5100. This infrared radiation is absorbed by water in the aerosol particles. This energy is then dispelled as the latent heat of evaporation. Also the second infrared reflector 6003 placed or the opposite side of the evaporation chamber enhances the transfer of infrared energy to the aqueous aerosol particles in transit through the evaporation chamber 5100.

The Counter-Flow Tube

The evaporation chamber 5100 also contains the counter-flow tube 1102 (see FIG. 1 and FIG. 5A). The counter-flow tube is positioned in receptacle 4041 (see FIG. 4C and FIG. 5A) with a small plate 5029 (see FIG. 5C) attached to the counter-flow tube positioned in a slot 5031 in the pillar 4040 (see FIG. 4C) of the manifold 1020. This tube, which receives gas from the flow divider, 5052 (see FIG. 5A) has a 180 degree bend followed by a short straight section. The curvature of this bend is such that when the small plate 5029 (see FIG. 5C) is correctly inserted into the slot 5031 in the manifold 1020 the port 5026 of the counter-flow tube is precisely coaxial with the center of the chamber and the orifice of the aerosol nozzle 1024.

The compressed gas from the flow divider 5052 flows through the counter-flow tube and exits the counter-flow port 5026. The jet of gas so created is coaxial with but of opposite direction to the aerosol plume. The short straight section of the counter-flow tube 1102 ensures a symmetrical jet of counter-flow gas. The flow rate in this gas jet is such that the aerosol plume 2106 is arrested midway 5300 between the nozzle orifice and the port 5026 of the counter-flow tube 1102.

The Aerosol Concentrator

Figure 7A:
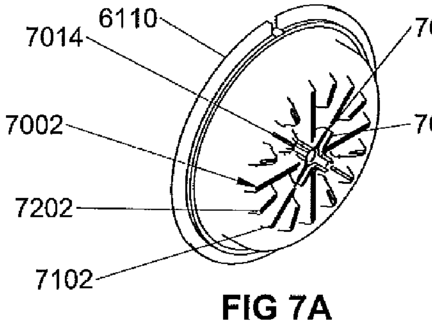
FIG. 7A show a perspective view of the output side of the acceleration pate illustrating the differences in nozzle length and sculptured design as well as a centrally located female indented cross for precise alignment of this acceleration plate with a raised cross on the deceleration plate.
Figure 7B:
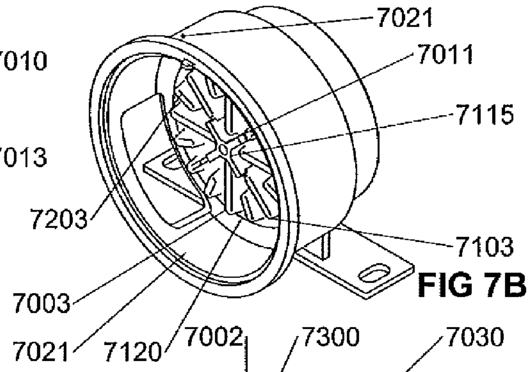
FIG. 7B shows a perspective view of the input side of the deceleration plate showing the respective differences in deceleration nozzle lengths and sculptured design as well as the male raised cross for precise alignment of the deceleration plate with the acceleration plate. A cowling surrounding the deceleration plate is also shown.
Figure 7C:
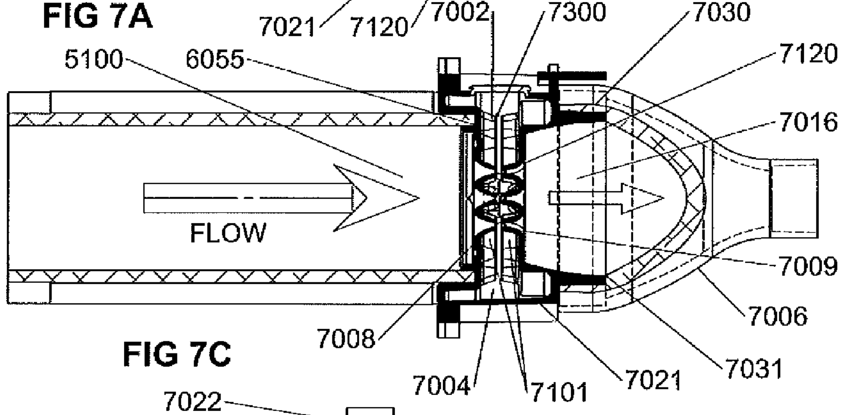
FIG. 7C shows a longitudinal section denoted as section K-K in FIG. 7D of the evaporation chamber, concentrator and aerosol output cone as indicated in FIG. 7D showing the interrelationships of these components.
Figure 7D:
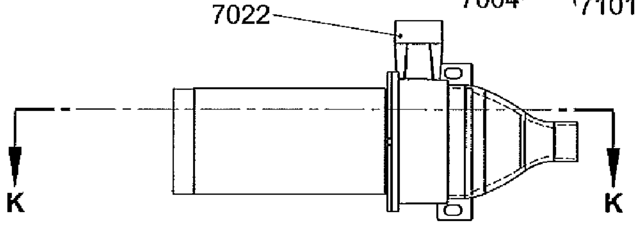
FIG. 7D shows a side view of the section of the evaporation chamber, concentrator and output cone illustrated in FIG. 7C.
Figure 7E:
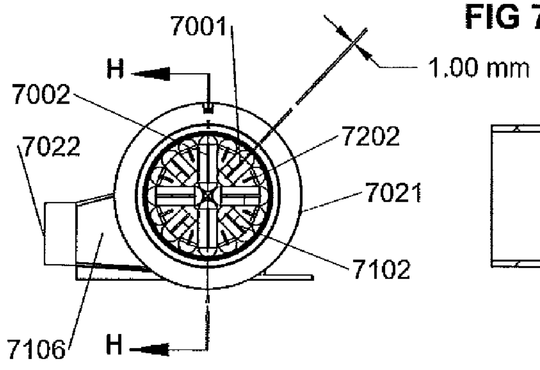
FIG. 7E shows a sectional rear view of the evaporation chamber, concentrator and output cone illustrated in FIG. 7F. It also illustrates the sculptured exhaust gas cone and port.
Figure 7F:
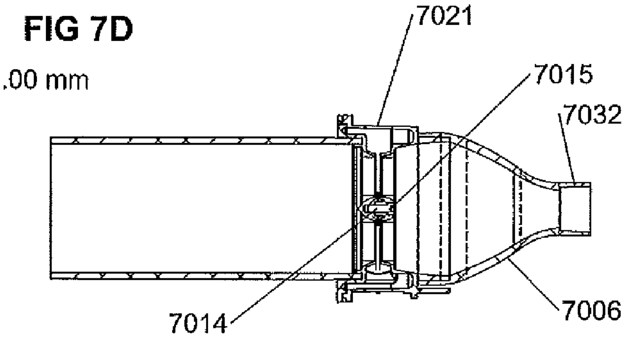
FIG. 7F shows a longitudinal section denoted H-H in FIG. 7E of the evaporation chamber, concentrator and output cone.

The virtual impactor shown in detail in FIGS. 7A, 7B, 7C, 7D, 7E and 7F is used to concentrate the output aerosol from the evaporation chamber 5100. As shown In FIG. 7C, the borosilicate/quartz tube of the evaporation chamber 5100 forms a snug fit into the circumferential groove 6055 in the acceleration plate 6110 of the virtual impactor 6100. Turning back to FIG. 7A, the virtual impactor is comprised of the acceleration plate 6110 containing long acceleration slit nozzles 7002, medium slit nozzles 7102 and short acceleration slit nozzles 7202 and a virtual impaction deceleration plate 7120 (see FIG. 7B) containing long 7003 and medium 7103 and short 7203 complementary deceleration slit nozzles. Attached to a deceleration plate 7120 is an exhaust gas cowling 7021 and exhaust port 7022 (see FIGS. 7D and 7E). A plenum 7004 formed by the acceleration face plate 6110, the deceleration plate 7120 and the exhaust gas cowling 7021 provides a low resistance flow path for the exhaust gas that emanates from a gap 7300 between the tips of the acceleration nozzles 7002, 7102, 7202 and the receptor slits on the deceleration nozzles 7003, 7103 and 7203. The acceleration plate 6110 fits snuggly into the virtual impactor deceleration plate 7120 such that the long 7002, medium 7102 and short 7202 acceleration nozzles are accurately aligned with the long 7003 and medium 7103 and short 7203 deceleration nozzles, respectively. There is a small gap 7300 between the orifices of these acceleration nozzles and the complementary deceleration nozzles. The slits of the acceleration nozzles are 1.1 mm wide. The receptor slits are 1.4 mm wide and positioned such that the gap 7300 between the between the slits of the acceleration nozzles and the deceleration nozzles is 1.3 mm. These are mentioned as a practical solution but are not intended to exclude other similar dimensions. To prevent particles entrained in the exhaust gas from entering the atmosphere, a filter (not shown) may be attached on the exhaust port 7022.

Although virtual impactor aerosol concentrators have previously been described, this concentrator has specific novel features which make the invention ideally suited to its proposed function. The concentrator was optimized to deliver the largest mass fraction of respirable aerosol generated by the nozzle 1024 (see FIG. 1) to the output. The concentrator is thus optimized to work best within the respiratory range, i.e. 1 to 5 micron aerodynamic diameter. Thus, for the purposes of this invention, this output aerosol can be considered to comprise of particles greater than 0.5 micrometers aerodynamic diameter. Thus, the virtual impactor should concentrate as many particles as possible which are smaller than or equal to 5 micrometers aerodynamic diameter. This, together with the requirements for a minimal pressure drop across the concentrator and the absence of any negative gas pressure to remove the exhaust gas from the gaps between the nozzles and the receiving slits required several novel design features to be incorporated.

1. The sixteen acceleration slit nozzles 7002, 7102 and 7202 are arranged radially as shown in FIG. 7A. The design is chosen so the exhaust gas exits the concentrator radially with minimal interference with the jet of aerosol passing between the acceleration nozzles 7002, 7102 and 7202 and the deceleration nozzles 7003, 7103, 7203 The shorter slit nozzles 7102, 7202 are designed to keep the flow across the evaporation chamber and the concentrator as uniform as possible. Note this configuration also maximizes the total cumulative length of the slits of the acceleration and deceleration nozzles. The total cumulative length of the accelerator nozzles is a preferred design is 18 cm although other cumulative lengths from 10 to 25 cm are possible.

2. The tapered surfaces of the input of the acceleration nozzles are designed with parabolic profiles 7008 (see FIG. 7C) to minimize the pressure differential required to accelerate the aerosol to nozzle velocity while minimizing aerosol deposition on the face of the acceleration plate 6110 of the concentrator 6100.

3. Likewise, the output cones of the deceleration nozzles 7003, 7103 and 7203 also are parabolically sculptured, having parabolic-like profiles 7009 (see FIG. 7C) to lower the resistance though the concentrator and minimize the turbulence of the aerosol at the output of the concentrator.

4. In addition, the downstream surfaces of the acceleration nozzles 7002, 7102 as well as the upstream surfaces of the deceleration nozzles 7003, 7103 are sculptured to lower the resistance of the exhaust gas between these nozzles. The sculptured shape leaves a gap of 1 cm or even more between the acceleration plate and deceleration plate at those locations where the sculptured acceleration and deceleration channels are not provided, i.e. leaves wide radial channels for the separated exhaust volume flow of low particle concentration to flow through these channels towards the cowling and eventually leave the system through the exhaust port 7022 (see FIG. 7E). Again, this enables the exhaust volume flow to be removed with minimal perturbation of the aerosol jets. The contours of these upstream and downstream surfaces which are designed to minimize both flat surfaces and sharp acute angles are critical to the overall performance of the concentrator. Of note, the downstream contours of the deceleration nozzles were shown to markedly increase the efficiency of the concentrator compared to slits within a flat virtual impaction plate.

5. To facilitate precise alignment of the acceleration nozzles 7002, 7102, 7202 with their respective deceleration nozzles, 7003, 7103, 7203, a location cylinder 7010 (see FIG. 7A) and a close fitting male cylinder 7011 ensure the coaxial alignment of the concentrator jet plate with the receptor plate. This together with a male cross 7115 and close fitting female cross shaped receptacle 7013 ensure that the jet slits are aligned precisely with the receptor slits of the deceleration nozzles.

6. The acceleration plate 6110 and deceleration plate 7120 are easily separable using a centrally placed heli-coil 7014 and screw 7015 (see FIG. 7F). This facilitates multiple assemblies and disassemblies and the cleaning of any aerosol deposited on the inner surfaces of the plates.

7. A cavity 7016 (see FIG. 7C) on the downstream side of the concentrator is designed to allow the turbulence from the receptor slits to decay and thus reduce unwanted aerosol deposition on the output cone.

8. The cowling 7021 (see FIG. 7E) has a sculptured exit channel 7106 and the exhaust port 7022 has a standard 22 mm taper which facilitates the connection of a disposable filter (not shown).

The aerosol at the output of the evaporation chamber 5100 is concentrated using the virtual impactor shown in FIGS. 7A, 7B, 7C, 7D, 7E and 7F. The aerosol from the evaporation chamber 5100 is accelerated as it passes through the acceleration nozzles 7002 and 7102 and 7202. In this case, the resistance to flow is minimized by using the long 7002 medium 7102 and short 7202 slit nozzle configuration. As the aerosol particles have considerably higher momentum than the gas and water vapor molecules in which they are suspended, the particles cross the gap 7300 and enter the deceleration nozzles 7003, 7103 and 7203. The aerosol flow rate of the output of the concentrator is generally only $1/5^{th}$ to $1/10^{th}$ that of the input flow rate. The gas flow rate difference between the input gas flow rate and the output gas flow rate is exhausted through the gap 7300 (see FIG. 7C) between the slits and into the plenum 7004. The concentrated aerosol at the output is funneled through an aerodynamically designed output cone 7006 to be delivered to the patient or for other desired purposes.

In a preferred configuration, on an outer wall of the output the cavity 7016 of the concentrator there is 1 to 2 cm broad flange 7030. This facilitates the placement of the output cone 7006 which has a matching internal diameter at its inlet and a step 7031 so that there are no flow discontinuities. The output of the cone has a standard 22 mm respirator taper 7032 (see FIG. 7F) to permit easy connection to an inhalation tube or filter (not shown).

EXAMPLES

The flow resistance of the dilution heater was found to be 0.12, 0.3 and 0.5 inches of water at 100, 150 and 200 liters per minute, respectively.

The flow resistance of the flow conditioner was determined to be 1 inch of water at 150 liters per minute and 1.8 inches of water at 200 liters per minutes. The flow resistance of the aerosol concentrator was determined to be less than 1 mm of water at all tested input flow rates below 300 liters/minute when the concentrator output flow rate was 40 liters per minute. The pressure inside the evaporation chamber was 0.3, 0.8, 1.4, 2.2 and 2.7 inches of water at chamber flow rates of 100, 150, 200, 250 and 300 liters/minute, respectively when the output flow rate of the concentrator was 40 liters/min.

A solution of 16% bovine serum albumin was fed to the nozzle using an infusion pump and aerosolized at 1 ml/minute. The nozzle pressure was 20 to 24 psi and the dilution gas flow 200 liters/minute. The resultant dry aerosol downstream from the concentrator was measured for two minutes at 40 liters/minute. The mass collected was determined gravimetrically. Typically 180 to 210 mg was collected. Thus the output of the device is about 100 mg per minute.

The overall efficiency of the throughput of the device was found to be 64%. The efficiency of the concentrator alone was found to be 85%.

Red food dye number 4 (0.2%) was added as a tracer to the 16% albumin solution. Under similar conditions an albumin aerosol was sampled at 30 liters per minute by a Marple Miller cascade impactor. Each stage of the impactor was washed 3 times with water and the relative mass on each stage was determined spectrophotometrically at 508 nanometers. The cumulative mass was plotted on log-probability paper. The mass median diameter was found to be 3.4 μm. Eighty five percent of the collected aerosol was found to be in the respirable range, i.e. the sum of all stages up to and including 5 micron.

To determine if the aerosolized protein was degraded by passing through the nebulizer, porcine trypsin was aerosolized and collected. A solution of this trypsin was placed on a confluent cell culture. The cells were seen to detach from the substrate. No difference could be seen between the results of a similar concentration of trypsin which has not been aerosolized.

To evaluate the shape and surface characteristics of the albumin particles produced, particles at the output were collected on a 12 mm diameter Millipore filter. The filter was placed at the center of a larger filter with similar flow characteristics. This filter was then mounted on an electron microscope stud and stored upright in a desiccator. Each sample was sputtered with palladium-gold and random images recorded on a Scanning Electron Microscope (SEM) at magnification of 1500. The albumin particles were found to be spherical with a smooth surface.

The embodiments described in the specifications of this disclosure provide practical compact portable devices for the generation of dry concentrated respirable particles from and liquid solution or suspension. This present disclosure provides the means, in a small practical clinical device, to generate and by dilution and heating, rapidly evaporate aqueous aerosols and thereafter to concentrate the resultant particles and deliver them at flow rates compatible with the full range of normal inspiratory flows.

Herein are described the inclusion of many valuable features in the embodiments which i. enable improved function, ii. facilitate the practical use of the embodiments and iii. have clinical advantages.

Among other advantages, the embodiment of the invention achieves the following:

a) Provides from a source directly adjacent to the evaporation chamber, localized radiant heat to the newly formed aqueous aerosol particles at the wavelengths of the maximum infrared absorption for water.

b) Allows the device to be used with different nozzle-holder configurations and for these to be easily interchangeable. These nozzle-holders enable either compressed gas delivered to a central orifice or around a central fluid stream. These nozzle-holders are keyed to the flow conditioner and may or may not include a compressible fluid reservoir.

c) Provides the means for a heated high velocity gas counter-flow stream in one direction as well as a uniform lower velocity flow in the opposite direction while allowing for the perturbations caused by an aerosol plume and counter-flow gas. This is achieved with minimal pressure drop using a two stage flow conditioner.

d) Efficiently concentrates a respirable aerosol with minimal pressure drop between the input and the exhaust gas using a variable length slit concentrator with radial input slits about 1.1 mm wide and output slits 1.4 mm wide with both input and output cones being parabolic in nature on both upstream and downstream surfaces.

e) Minimizes any aerosol deposition due to turbulence at the output of the concentrator by including a cavity to allow these vortexes to relax.

f) Provides an efficient means of delivering the concentrated aerosol at the output by utilizing an internally parabolic-shaped output cone.

g) Eliminates high pressure couplings on large diameters so the device can be easily assembled and disassembled for cleaning.

h) Lowers the resistance to gas flow so as to enable the construction of a small device using a small blower to provide the dilution gas.

i) Minimizes leakage of gas and/or aerosol between the various components of the device while maintaining structure integrity junction between each of the components by including at least two and preferably 3 or 4 mutually perpendicular surfaces.

j) Facilitates the provision of a removable counter-flow gas that is precisely coaxial with the aerosol plume and of opposite direction to the aerosol plume a counter-flow tube was keyed into a flow conditioner.

k) Provides heated compressed gas to both the nozzle and the counter-flow tube while minimizing heat losses by incorporating a flow divider and flow regulating orifice into the flow conditioner.

l) Facilitates easy and precise assembly and disassembly the concentrator plates by having a raised male cylindrical protrusion and cross and reciprocal female indents in the center of the concentrator. These provide both axial and rotational high precision alignment.

m) Prevents any aerosol particles in the exhaust gas stream from contaminating the atmosphere by use of a cowling and filter port.

n) Provides a concentrated aerosol at a small positive pressure as pressure-assist for patients who have trouble generating sufficient inspiratory pressure and flow to trigger some other dry powder inhalers.

o) Generates dries and concentrates near sterile aerosols by the use of sterilizable components of the embodiments together with the positive pressure inside the device.

In the following, the embodiment according to the present invention is summarized.

Generation of an Aerosol

The liquid to be aerosolized is fed into the connector 2005 in the nozzle holder and conducted via channels to the nozzle 1024. The compressed gas required to aerosolize a liquid to be aerosolized is provided to fitting 1019. It passes though the heater 1011 where it is warmed to the temperature required. This temperature is measured with the thermocouple and the heater regulated using a PID controller. This heated gas is divided into two flows. One flow is directed though a flow limiting orifice 5024 to the counter-flow tube 1102. The remaining flow proceeds into the annular groove 4071 and from there into the barrel ports 2008, 3008 and thence to the nozzle 1024. The interaction of the liquid to be aerosolized and the high pressure gas in the nozzle causes the production of a plume 2106 of liquid aerosol. This warm gas in the counter-flow tube is directed into the aerosol plume coaxial with but in opposite direction to the plume. This gas flow arrests the aerosol plume midway between the nozzle and the end of the counter-flow tube. The injection of this heated gas into the aerosol plume enhances the rapid evaporation of the liquid solvent.

As Shown in FIG. 1 the aerosol processing system contains two gas heaters, one gas heater 1011 to warm the compressed gas to generate the aerosol and provide a counter-flow 5120 (see FIG. 5A) to arrest the aerosol plume 2106 and the other gas heater 1004 to warm the gas to dilute the aerosol. These warm gas flows are distributed to their respective functions within a flow-conditioner. Within the flow conditioner manifold 1020 (see FIG. 5A), the compressed warm gas is divided into two components, one is routed through the nozzle barrel 2001 of the nozzle holder to generate the aerosol at the tip of the nozzle and the other to form the counter-flow gas stream 5120 coaxial with but of opposite direction to the nozzle plume 2106. The evaporation of the aerosol as it transits an evaporation chamber 5100 is augmented by the use of a radiant heater 6001 together with its associated 6002 and 6003 reflectors. The aerosol is accelerated through nozzles 7002, 7102 and 7202 in the acceleration plate 6110 (see FIG. 7A) of the low resistance virtual impactor. The particles that have a much higher momentum than the gas molecules traverse a gap and pass through the slits of the deceleration nozzles, 7003, 7103 and 7203 in the deceleration plate 7120 into the output collection cones. When the aerosol flow rate at the output of the virtual impactor is lower than the flow rate when entering the virtual impactor, the residual gas is exhausted between the acceleration plate 6110 and deceleration plate 7120. The majority of the particles pass through the slits in the deceleration plate 7120 and thus comprise the output aerosol.

Schematics of the gas input and conditioning components of the invention are depicted in FIG. 1. An optional gas drying chamber 1002 is provided for use as needed. The chamber of this dryer is filled with the desiccant 1003. A miniature blower 1001 is connected, through the flow measurement device 1023 to a dilution gas heater 1004. This heater 1004 is connected via the right angle fitting 1013 to the inlet 4028 on the flow conditioner manifold 1020. A thermocouple (not shown) is situated in the lumen of this right angle fitting. The flow conditioner has the two donut shaped channels 5021, 5022 separated by the flow partitioner 5103 with slots 5012 that allow gas to pass from one channel 5021 to the other channel 5022. The second stage of the flow conditioner is connected to an evaporation chamber 5100 through the holes 5013, 5023 in this second flow conditioner 5102. The evaporation chamber 5100 is positioned between the flow conditioner manifold 1020 and an aerosol concentrator 6110. The aerosol concentrator has radially arranged acceleration nozzles 7002, 7102, 7202 which also are connected to the exhaust plenum 7004. The deceleration nozzles 7003, 7103 and 7203 are in close proximity to and are aligned with the acceleration nozzles 7002, 7102 and 7202, respectively. The downstream ends of these deceleration nozzles are contiguous with the turbulence decay cavity 7016 and aerosol collection and cone 7006. This collection cone is connected to an output device or person (not shown) that regulates the output flow as desired.

Compressed gas is provided to fitting 1019. This fitting is connected to the compressed gas heater 1011. This is connected to an input port 4028 on the flow conditioner manifold 1020. This port 4028 is connected to a flow divider. One side of this divider is connected via a flow limiting orifice 5024 to the counter-flow tube 1102. The other side of this divider is connected to an annular groove 4071. This annular groove interfaces with ports 2008 on the nozzle holder. These ports are connected through channels to the nozzle 1024. The fluid connector 2005, in a preferred configuration is a Luer fitting. This connector 2005 is connected though channels to the nozzle 1024.

The invention incorporates a novel easily replaceable integral nozzle holder and nozzle 1024. The barrel 2001, 3001 of this nozzle holder is inserted into the cylindrical receptacle 4030 along the center axis of the flow conditioning manifold 1020. As noted, a circumferential groove 4071 in this manifold is contiguous with ports 2008 on the barrel on the nozzle holder.

The gas to dilute and help evaporate the liquid aerosol is provided by a small blower 1001. The flow of this gas is measured as it passes though the flowmeter 1023. This gas is heated as it passes through the heater 1004. This high velocity warm gas passes through the right angled channel 1007 to the inlet 5122. This gas flow is transformed into a flow of relatively uniform velocity as it passes though the pressure equalization chambers 5021, 5222 and the flow partitioners 5103, 5102. This high velocity dilution gas is transformed by this very low resistance flow conditioner to provide an even gas flow in the evaporation chamber 5100 such the velocity of the output aerosol as it enters the acceleration plate 6110 (see FIG. 6A) of the virtual impactor illustrated in FIGS. 7A, 7B, 7C, 7D, 7E, 7F is relatively uniform.

The aerosol is entrained within and further evaporated by the dilution gas as it flows through the evaporation chamber. This evaporation is augmented by the infrared radiation from the infrared lamp 6001. The now solid phase aerosol enters the acceleration nozzles 7002, 7102, 7202 to form aerosol jets. Most of the aerosol in these jets enters the deceleration nozzles 7003, 7103, 7203 and is presented to the output cone 7006. Most of the gas (which has much less momentum than the particles) is exhausted through the exhaust plenum 7004.

To facilitate rapid drying of the aqueous aerosol in a confined space, the aerosol plume from the compressed gas-powered nozzle is preferably arrested and mixed with dilution gas. This dilution gas should be warmed. US Patent application 200701445 teaches the use of a coaxial counter-flow jet to arrest an aerosol plume. However, neither was the jet gas nor the counter-flow gas heated; let alone to over 100 degrees Celsius. This hot gas provides the latent heat of evaporation to facilitate extremely rapid evaporation of the aerosol droplets. Notwithstanding this high input gas temperature, the temperature within the plume is generally less than 30° C. The particles are cooled by the latent heat of evaporation. Thus the provision of this hot gas does not result in the denaturing of any protein in the aerosol generated Horizontal System The virtual impactor concentrator described in US Patent application 200701445 has a cut-off of 2.5 micrometers. That prior art system obviated the necessity of collecting and re-suspending the dry power mixture; a time consuming and potentially wasteful procedure. However, that liquid to dry powder aerosol generator used up to 300 liters of dilution gas at relatively high pressure (20-50 psi). This required a 5 horsepower compressor and a tank of pressurized gas. Such a large and expensive compressors and/or the access to large compressed gas tanks makes that prior art device impractical for home use.

Some of the novel features of the system according to the present invention are the flow conditioner and the virtual impactor and the exchangeable cartridge/nozzle. In addition, further advances were achieved by reducing the pressure drops through the gas heaters and the inter-connecting parts.

This facilitates the generation, dilution, evaporation and concentration of protein aerosol with a density less than 1 which provides a highly concentrated aerosol of particles of a size of about 1 micrometer and above for delivery to the respiratory tract. This is a compact device whose dilution gas can be at a pressure drop in the entire volume flow of only 1-3 inches of water through the device downstream from the dilution air blower. This requires a substantial reduction of the pressure drops inherent within the previous system US patent application publication no. 200701445.

What is claimed is:

1. A nozzle for generating an aerosol from a fluid and a gas, the nozzle comprising:

a cone having at least one wettable cone-shaped gas exit channel that widens in a direction of gas flow from a cone apex to a cone base where a lip is provided on the cone, said wettable cone-shaped gas exit channel being connected at the cone apex by an orifice to a nozzle gas supply channel forming an aerosolizing perimeter between the orifice and the cone; and at least one annular fluid exit port encompassing the lip at the cone base, said cone base being connected to a nozzle fluid supply channel so that the fluid to be aerosolized flows from the nozzle fluid supply channel by capillary forces and by negative pressure created by a jet of gas exiting the orifice, the fluid flowing from the annular fluid exit port over the lip of the cone towards the apex of the cone where it is aerosolized at the aerosolizing perimeter.

2. The nozzle according to claim 1, further comprising:

a cylindrical stem having an outer stem wall having an outer stem diameter; and an annulus having an annulus hole wall comprising an inner annulus diameter that is slightly larger than the outer stem diameter; wherein the cylindrical stem extends through the annulus hole and comprises the wettable cone-shaped gas exit channel; and the annular fluid exit port is formed by an annular gap between the annulus hole wall and the outer stem wall.

3. The nozzle according to claim 2, wherein a diameter difference between the inner annulus diameter and the outer stem diameter is between 0.006 and 0.8 mm resulting in an annular gap width between the 0.003 and 0.4 mm.

4. The nozzle according to claim 2, wherein the annulus comprises a front face that extends substantially perpendicular to the annular fluid exit port.

5. The nozzle according to claim 4, wherein the stem protrudes by 0-1 mm beyond the front face of the annulus.

6. The nozzle according to claim 4, wherein the front face of the annulus is hydrophobic while the outer stem wall is readily wettable by the fluid.

7. The nozzle according to claim 2, wherein a diameter of the cone base of the wettable cone-shaped gas exit channel equals substantially the entire outer stem diameter so that the annular lip at which the stem terminates at the cone base of the wettable cone-shaped gas exit channel is a sharp annular lip.

8. The nozzle according to claim 1, wherein the cone-shaped gas exit channel subtends an angle between 15 and 80 degrees.

9. The nozzle according to claim 8, wherein the cone base comprises a diameter between 1 and 2 mm.

10. The nozzle according to claim 1, wherein the nozzle gas supply channel comprises a diameter is between 0.05 mm and 1 mm.

11. A nozzle holder comprising a first end with a nozzle holder fluid inlet port and a second end comprising the nozzle according to claim 1, the nozzle holder further comprising:

a barrel with an inner cylindrical barrel hole and an inner cylindrical barrel diameter; and a nozzle body comprising the stem and a cylindrical crown comprising an outer cylindrical crown surface snugly fit into the cylindrical barrel hole wall; wherein the cylindrical crown comprises a plurality of circumferentially spaced grooves that are connected to the annular fluid exit port.

12. The nozzle holder according to claim 11, wherein the nozzle body comprises a cylindrical nozzle body base having an outer cylindrical nozzle body base surface comprising an outer nozzle body base diameter, wherein an annular fluid supply channel is formed between the outer cylindrical nozzle body base surface and the cylindrical barrel hole wall.

13. The nozzle holder according to claim 12, wherein the barrel comprises radial gas supply channels feeding gas to a central gas supply channel that is connected to the nozzle gas supply channel and comprises a diameter that is several times larger than that of the nozzle gas supply channel.

14. The nozzle holder according to claim 11, wherein the nozzle holder is designed as a disposable part that comprises in close proximity to the first end of the nozzle holder a knob for inserting and removing the nozzle holder into or from a receptacle of an aerosol generator.

15. The nozzle holder according to claim 14, wherein the barrel comprises an outer cylindrical surface that is adapted to fit snugly into the receptacle of an aerosol generator.

16. The nozzle holder according to claim 15, wherein the nozzle holder fluid inlet port is a Luer fitting that is adapted to receive a disposable fluid cartridge.

17. The nozzle holder according to claim 16, wherein the nozzle holder and the fluid cartridge are pre-assembled as one disposable unit.

* * * * *